United States Patent [19]

Englert et al.

[11] Patent Number: 5,811,448

[45] Date of Patent: Sep. 22, 1998

[54] SUBSTITUTED CHROMANYSULFONYL (THIO) UREAS, PROCESSING FOR THEIR PREPARATION AND PHARMACEUTICAL USES THEREOF

[75] Inventors: Heinrich Christian Englert, Hofheim; Uwe Gerlach, Hattersheim; Dieter Mania, Königstein; Wolfgang Linz, Mainz; Heinz Gögelein, Frankurt; Erik Klaus, Kelkheim; Peter Crause, Offenbach, all of Germany

[73] Assignee: Hoechst Aktiengesellschaft, Frankfurt am Main, Germany

[21] Appl. No.: 760,610

[22] Filed: Dec. 4, 1996

[30] Foreign Application Priority Data

Dec. 14, 1995 [DE] Germany .................. 195 46 736.1

[51] Int. Cl.$^6$ .................. A61K 31/35; A61K 31/40; C07D 311/60; C07D 407/12

[52] U.S. Cl. .................. 514/422; 514/212; 514/309; 514/320; 514/414; 514/456; 540/524; 546/141; 546/196; 548/472; 548/525; 549/407

[58] Field of Search .................. 549/407; 514/456, 514/422, 212, 309, 320, 414; 548/517, 454, 525; 540/524; 546/141, 196

[56] References Cited

U.S. PATENT DOCUMENTS

| | | | |
|---|---|---|---|
| 3,780,027 | 12/1973 | Cargoe et al. | 549/494 |
| 3,803,176 | 4/1974 | Christensen et al. | 549/405 |
| 5,091,394 | 2/1992 | Englert et al. | 514/331 |
| 5,140,039 | 8/1992 | DeBarbardus et al. | 514/422 |
| 5,185,364 | 2/1993 | DeBarbardus et al. | 514/444 |
| 5,292,755 | 3/1994 | Englert et al. | 514/331 |
| 5,294,608 | 3/1994 | Lang et al. | 514/108 |
| 5,364,868 | 11/1994 | Englert et al. | 514/331 |
| 5,373,024 | 12/1994 | Lang et al. | 514/618 |
| 5,416,954 | 5/1995 | Lal et al. | 514/307 |
| 5,516,805 | 5/1996 | Lang et al. | 514/620 |
| 5,547,953 | 8/1996 | Weichert et al. | 514/226.5 |
| 5,574,069 | 11/1996 | Englert et al. | 514/586 |

FOREIGN PATENT DOCUMENTS

| | | |
|---|---|---|
| 3301393 | 8/1993 | Australia . |
| 3301493 | 8/1993 | Australia . |
| 3301593 | 8/1993 | Australia . |
| 5271693 | 12/1993 | Australia . |
| 4163593 | 1/1994 | Australia . |
| 4746093 | 3/1994 | Australia . |
| 5236893 | 6/1994 | Australia . |
| 5249093 | 6/1994 | Australia . |
| 5522994 | 8/1994 | Australia . |
| 6454394 | 12/1994 | Australia . |
| 6454494 | 12/1994 | Australia . |
| 4221896 | 2/1995 | Australia . |
| 6881194 | 2/1995 | Australia . |
| 6884494 | 2/1995 | Australia . |
| 7022394 | 2/1995 | Australia . |
| 7039794 | 3/1995 | Australia . |
| 7150794 | 3/1995 | Australia . |
| 1135395 | 8/1995 | Australia . |
| 1635495 | 10/1995 | Australia . |
| 1786195 | 11/1995 | Australia . |
| 1799995 | 11/1995 | Australia . |
| 664940B | 12/1995 | Australia . |
| 2172095 | 1/1996 | Australia . |
| 2330095 | 1/1996 | Australia . |
| 3050495 | 3/1996 | Australia . |
| 3050595 | 3/1996 | Australia . |
| 3050695 | 3/1996 | Australia . |
| 3900895 | 5/1996 | Australia . |
| 2168315 | 1/1996 | Canada . |
| 0325964 | 8/1989 | European Pat. Off. . |
| 0727416 | 2/1996 | European Pat. Off. . |
| 1518874 | 5/1970 | Germany . |
| 0727417 | 2/1996 | Germany . |
| 1314325 | 4/1973 | United Kingdom . |
| 9426709 | 11/1994 | WIPO . |

OTHER PUBLICATIONS

Duff, Henry J. et al., *Circulation*, 79(6), 1257–63 (1989).

*Eur. Heart of J.* 9(suppl. 1):25 and 167 (1988) book of abstracts.

Schmid, Andreas et al. *Biochemical and Biophysical Research Comm.* 112–117 (1992).

Scholz, Wolfgang et al. *Cardiovascular Res.* (1995) 29(2):260–8.

Rosskopf, Dieter et al. *Cellular Physiology Biochem* (1995), (5)4, 269–275.

Scholz, Wolfgang et al. *Basic Research Cardiology* 1993, 88(5), 443–55.

Sack, Stefan et al. *J. Cardiovasc. Pharmacol.* (1994)23(1), 72–78.

Kranzhofer, Roger et al. *Circ. Res.* (1993), 73(2), 264–8.

Scholz, Wolfgang et al. *Br. J. Pharmacol.* (1993), 109(2), 562–8.

(List continued on next page.)

*Primary Examiner*—Richard L. Raymond
*Attorney, Agent, or Firm*—Finnegan, Henderson, Farabow, Garrett & Dunner L.L.P.

[57] ABSTRACT

Substituted chromanylsulfonyl(thio)ureas, processes for their preparation, their use in pharmaceutical preparations, and pharmaceutical preparations comprising them Chromanylsulfonyl(thio)ureas of the formula I $$R(3)-\overset{H}{N}-\overset{Z}{\underset{}{\|}}-\overset{H}{N}-\overset{O}{\underset{\|}{S}}-\underset{R(1)}{\text{Ar}}-\overset{R(2a)}{\underset{}{\text{C}}}\overset{O}{\underset{\|}{-A}}\overset{NH}{\underset{R(2e)}{\text{O}}}\overset{R(2b)}{\underset{R(2d)}{R(2c)}}$$ (I)

are useful pharmaceuticals for the treatment of cardiac arrhythmias and for the prevention of sudden heart death due to arrhythmia. They can be used as antiarrhythmics and are suitable for the prevention of sudden heart death, for the treatment of cardiac insufficiency and also heart failure as a result of the effects of shock.

47 Claims, No Drawings

OTHER PUBLICATIONS

Scholz, Wolfgang et al. *J. Mol. Cell. Cardiol.* (1992) 24(7), 731–39.

Scholz, Wolfgang et al. *Cardiovascular Research.* (Feb., 1995) vol. 29(2), 184–8.

*Biological Chemistry* Hoppe–Seyler (1991), vol. 372, No. 9, pp.750.

Faber, Sabine et al. *Cell. Physiol. Biochem* (1996), 6(1–2), 39–49.

Busch, Gillian L. et al. *Pfluegers Arch.* (1996), 431(5), 690–96.

Englert, Heinrich C. et al. *Eur. J. Pharmacol.* (1992), 210 (1), 69–75.

Mitsuka, Masayuki et al. *Circulation Research* (1993), vol. 73(2):269–275.

SUBSTITUTED CHROMANYSULFONYL (THIO) UREAS, PROCESSING FOR THEIR PREPARATION AND PHARMACEUTICAL USES THEREOF

DESCRIPTION

Substituted chromanylsulfonyl(thio)ureas, processes for their preparation, their use in pharmaceutical preparations, and pharmaceutical preparations comprising them The invention relates to substituted chromanyisulfonyl (thio)ureas of the formula I,

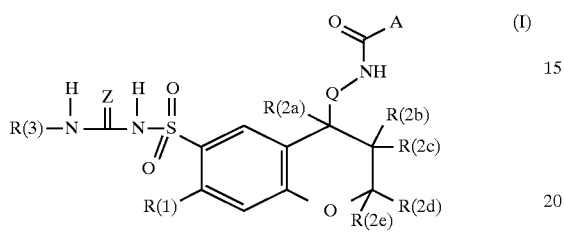

in which:

R(1) is hydrogen, alkyl having 1 to 4 carbon atoms, alkoxy having 1 to 4 carbon atoms, fluorine, chlorine, bromine, iodine, $CF_3$, $NH_2$, NH-alkyl having 1 to 4 carbon atoms, $N(alkyl)_2$ having 1 to 4 carbon atoms in the identical or different alkyl radicals, or S-alkyl having 1 to 4 carbon atoms;

R(2a) is hydrogen or alkyl having 1 or 2 carbon atoms;

R(2b) and R(2d), which are identical or different, are hydrogen, alkyl having 1 or 2 carbon atoms, unsubstituted phenyl, substituted phenyl, unsubstituted benzyl or benzyl substituted in the phenyl radical, up to three identical or different substituents, selected from the group consisting of hydrogen, halogen, alkyl having 1 or 2 carbon atoms and alkoxy having 1 or 2 carbon atoms being present as substituents in phenyl radicals;

R(2c) and R(2e), which are identical or different, are hydrogen or alkyl having 1 or 2 carbon atoms, R(3) is hydrogen, alkyl having 1, 2, 3 or 4 carbon atoms, cycloalkyl having 3, 4, 5 or 6 ring carbon atoms, $CH_2$-cycloalkyl having 3, 4, 5 or 6 ring carbon atoms, or $CF_3$;

Q is $(CH_2)_n$;

n is 1 or 2;

Z is sulfur or oxygen;

A is phenyl which is unsubstituted or substituted by up to three identical or different substituents selected from the group consisting of hydrogen, halogen, alkyl having 1 or 2 carbon atoms and alkoxy having 1 or 2 carbon atoms;

or

A is the radical of a saturated or unsaturated lactam of the formula

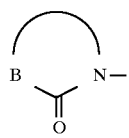

B is alkenylene or alkylene having 3, 4, 5 or 6 carbon atoms, which is unsubstituted or is substituted by up to three identical or different alkyl groups having 1, 2, 3 or 4 carbon atoms;

or

A is the radical of a bicyclic system of the formula

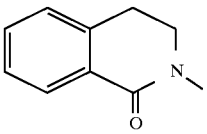

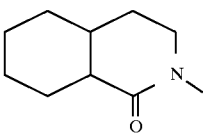

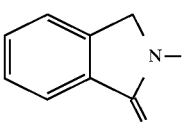

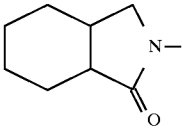

and their physiologically tolerable salts.

Preferred compounds of the formula I are those in which:

R(1) is hydrogen, alkyl having 1 or 2 carbon atoms, alkoxy having 1 to 4 carbon atoms, fluorine, chlorine, bromine, iodine or $CF_3$, R(2a), R(2b) and R(2d), which are identical or different, are hydrogen or alkyl having 1 or 2 carbon atoms;

R(2c) and R(2e) are hydrogen;

R(3) is hydrogen or alkyl having 1, 2, 3 or 4 carbon atoms;

Q is $(CH_2)_n$;

n is 1 or 2;

Z is sulfur or oxygen;

A is phenyl which is unsubstituted or substituted by up to three identical or different substituents selected from the group consisting of hydrogen, halogen, alkyl having 1 or 2 carbon atoms and alkoxy having 1 or 2 carbon atoms;

or

A is the radical of a saturated or unsaturated lactam of the formula

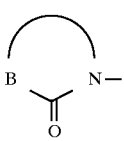

B is alkenylene or alkylene having 3, 4, 5 or 6 carbon atoms, which is unsubstituted or is substituted by up to three identical or different alkyl groups having 1, 2, 3 or 4 carbon atoms;

or

A is the radical of a bicyclic system of the formula

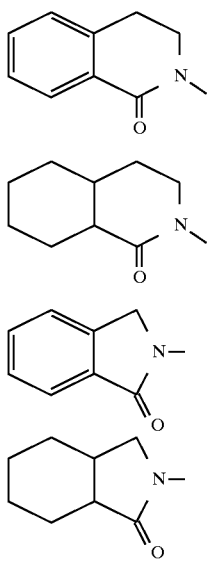

Particularly preferred compounds of the formula I are those in which:

R(1) is hydrogen, alkyl having 1 or 2 carbon atoms, alkoxy having 1 or 2 carbon atoms, fluorine, chlorine, bromine, iodine or $CF_3$;

R(2a), R(2b), R(2c), R(2d) and R(2e) are hydrogen;

R(3) is hydrogen or alkyl having 1, 2, 3 or 4 carbon atoms;

Q is $(CH_2)_n$;

n is 1 or 2;

Z is sulfur or oxygen;

A is phenyl which is unsubstituted or substituted by up to three identical or different substituents selected from the group consisting of hydrogen, halogen, alkyl having 1 or 2 carbon atoms and alkoxy having 1 or 2 carbon atoms;

or

A is the radical of a saturated or unsaturated lactam of the formula

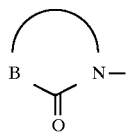

B is alkenylene or alkylene having 3, 4, 5 or 6 carbon atoms, which is unsubstituted or is substituted by up to three identical or different alkyl groups having 1, 2, 3 or 4 carbon atoms;

or

A is the radical of a bicyclic system of the formula

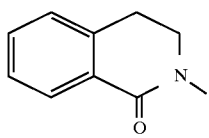

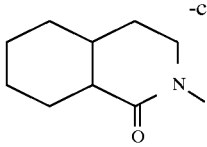
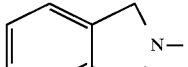
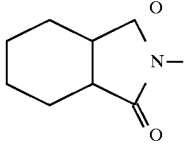

Very particularly preferred compounds of the formula I are those in which:

R(1) is hydrogen, alkyl having 1 or 2 carbon atoms or alkoxy having 1 or 2 carbon atoms;

R(2a), R(2b), R(2c), R(2d) and R(2e) are hydrogen;

R(3) is hydrogen or alkyl having 1, 2, 3 or 4 carbon atoms;

Q is $(CH_2)_n$;

n is 1 or 2;

Z is sulfur;

A is phenyl which is unsubstituted or substituted by up to three identical or different substituents selected from the group consisting of hydrogen, halogen, alkyl having 1 or 2 carbon atoms and alkoxy having 1 or 2 carbon atoms;

or

A is the radical of a saturated or unsaturated lactam of the formula

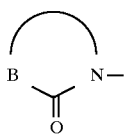

B is alkenylene or alkylene having 3, 4, 5 or 6 carbon atoms, which is unsubstituted or is substituted by up to three identical or different alkyl groups having 1, 2, 3 or 4 carbon atoms;

or

A is the radical of a bicyclic system of the formula

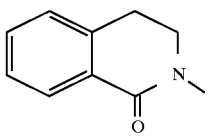
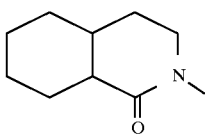

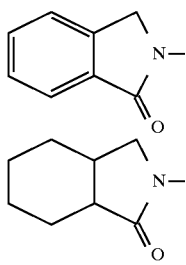

Very specifically preferred compounds of the formula I are those in which:

R(1) is hydrogen, alkyl having 1 or 2 carbon atoms or alkoxy having 1 or 2 carbon atoms;
R(2a), R(2b), R(2c), R(2d) and R(2e) are hydrogen;
R(3) is hydrogen, methyl or ethyl;
Q is $(CH_2)_n$;
n is 1 or 2;
Z is sulfur;
A is phenyl which is unsubstituted or substituted by up to three identical or different substituents selected from the group consisting of hydrogen, halogen, alkyl having 1 or 2 carbon atoms and alkoxy having 1 or 2 carbon atoms;

or

A is the radical of a saturated or unsaturated lactam of the formula

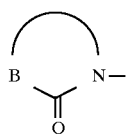

B is alkenylene or alkylene having 3, 4, 5 or 6 carbon atoms, which is unsubstituted or is substituted by up to three identical or different alkyl groups having 1, 2, 3 or 4 carbon atoms.

Very particularly specifically preferred compounds of the formula I are those in which:

R(1) is hydrogen, alkyl having 1 or 2 carbon atoms or alkoxy having 1 or 2 carbon atoms;
R(2a), R(2b), R(2c), R(2d) and R(2e) are hydrogen;
R(3) is hydrogen, methyl or ethyl;
Q is $CH_2$;
Z is sulfur;
A is phenyl which is unsubstituted or substituted by up to three identical or different substituents selected from the group consisting of hydrogen, halogen, alkyl having 1 or 2 carbon atoms and alkoxy having 1 or 2 carbon atoms.

Likewise very particularly preferred compounds of the formula I are also those in which:

R(1) is hydrogen, alkyl having 1 or 2 carbon atoms or alkoxy having 1 or 2 carbon atoms;
R(2a), R(2b), R(2c), R(2d) and R(2e) are hydrogen;
R(3) is hydrogen or alkyl having 1, 2, 3 or 4 carbon atoms;
Q is $(CH_2)_n$;
n is 1 or 2;
Z is oxygen;
A is phenyl which is unsubstituted or is substituted by up to three identical or different substituents selected from the group consisting of hydrogen, halogen, alkyl having 1 or 2 carbon atoms and alkoxy having 1 or 2 carbon atoms;

or

A is the radical of a saturated or unsaturated lactam of the formula

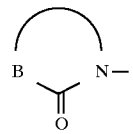

B is alkenylene or alkylene having 3, 4, 5 or 6 carbon atoms, which is unsubstituted or is substituted by up to three identical or different alkyl groups having 1, 2, 3 or 4 carbon atoms;

or

A is the radical of a bicyclic system of the formula

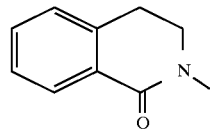

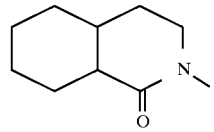

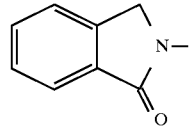

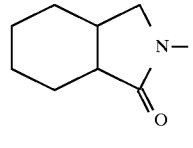

Likewise very specifically preferred compounds of the formula I are also those in which:

R(1) is hydrogen, alkyl having 1 or 2 carbon atoms or alkoxy having 1 or 2 carbon atoms;
R(2a), R(2b), R(2c), R(2d) and R(2e) are hydrogen;
R(3) is hydrogen, methyl or ethyl;
Q is $(CH_2)_n$;
n is 1 or 2;
Z is oxygen;
A is phenyl which is unsubstituted or is substituted by up to three identical or different substituents selected from the group consisting of hydrogen, halogen, alkyl having 1 or 2 carbon atoms and alkoxy having 1 or 2 carbon atoms, or A is the radical of a saturated or unsaturated lactam of the formula

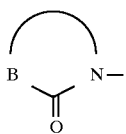

B is alkenylene or alkylene having 3, 4, 5 or 6 carbon atoms, which is unsubstituted or is substituted by up to three identical or different alkyl groups having 1, 2, 3 or 4 carbon atoms.

Likewise very particularly specifically preferred compounds of the formula I are also those in which:

R(1) is hydrogen, alkyl having 1 or 2 carbon atoms or alkoxy having 1 or 2 carbon atoms;

R(2a), R(2b), R(2c), R(2d) and R(2e) are hydrogen;

R(3) is hydrogen, methyl or ethyl;

Q is $CH_2$;

Z is oxygen;

A is phenyl which is unsubstituted or is substituted by up to three identical or different substituents selected from the group consisting of hydrogen, halogen, alkyl having 1 or 2 carbon atoms and alkoxy having 1 or 2 carbon atoms;

R(2a) is preferably hydrogen.

The term alkyl means, if not stated otherwise, straight-chain or branched saturated hydrocarbon radicals. This also applies to alkyl radicals which are contained in alkoxy radicals. Examples of alkyl radicals are methyl, ethyl, n-propyl, isopropyl, n-butyl, isobutyl, sec-butyl and tert-butyl. Examples of cycloalkyl radicals are cyclopropyl, cyclobutyl, cyclopentyl and cyclohexyl. Examples of alkylene and alkenylene radicals which are represented by the group B are 1,3-propylene, 1,4-butylene, 1,5-pentylene, 1,6-hexylene, 1,3-prop-1-enylene, 1,3-prop-2-enylene, 1,4-but-1-enylene, 1,4-but-2-enylene, 1,4-but-3-enylene, 1,5-pent-1-enylene, 1,5-pent-2-enylene, 1,5-pent-3-enylene and 1,5-pent-4-enylene. In substituted phenyl radicals which can occur as such or in benzyl radicals, the substituents can be located in any desired positions, in the case of monosubstitution, for example, in the ortho-, meta- or para-position, in the case of disubstitution in the 2,3-, 2,4-, 2,5-, 2,6-,3,4- or 3,5-position, in the case of trisubstitution, for example, in the 2,3,4-, 2,3,5-, 2,3,6- or 3,4,5-position. Halogen, if not stated otherwise, means fluorine, chlorine, bromine and iodine, preferably fluorine and chlorine.

Furthermore, compounds of the formula I having centers of chirality, for example on the carbon atoms 2, 3, 4 of the chroman system on appropriate substitution, can occur. In this case, the invention includes all possible stereoisomers, both enantiomers and diastereomers, and also mixtures of two or more stereoisomers in any desired ratios, enantiomers, for example, in enantiomerically pure form, the invention relating to both levo- and dextrorotatory antipodes, and also in mixtures of the two enantiomers in varying ratios.

The compounds of the formula I are useful pharmaceutical active compounds for human and veterinary medicine, in particular for the treatment of cardiac arrhythmias and decreased contractility of the heart. They can furthermore be used as intermediates for the preparation of further pharmaceutical active compounds.

For certain benzenesulfonylureas a blood sugar lowering action has been described. A prototype of such blood sugar lowering sulfonylureas is glibenciamide, which is used therapeutically as an agent for the treatment of diabetes mellitus and which serves in research as a highly regarded tool for the investigation of so-called ATP-sensitive potassium channels. In addition to its blood sugar lowering action, glibenclamide has yet other actions which to date can still not be employed therapeutically, but which are all attributed to blockade of precisely these ATP-sensitive potassium channels. These include, in particular, an antifibrillatory action on the heart. In the treatment of ventricular fibrillation or its preliminary stages, however, a simultaneous lowering of blood sugar would be undesirable or even dangerous, as it can further worsen the condition of the patient. European Offenlegungsschrift EP-A-612 724 discloses benzenesulfonylureas which have effects on the cardiovascular system; their effect, however, is still not satisfactory in many respects. Chromanyl derivatives are neither described nor suggested therein.

EP-A-325 964 describes chroman compounds as $\alpha_2$-adrenergic antagonists having action against depressions, metabolic disorders, glaucoma, migraine and high blood pressure. It does not describe, however, any compounds with substitution by sulfonylurea or sulfonylthiourea groups and also does not suggest the compounds according to the invention.

The invention furthermore relates to processes for the preparation of the compounds of the formula I, which comprise the reaction steps shown below.

(a) Chromanylsulfonylureas of the formula I, in which R(3) has a meaning other than hydrogen and Z is oxygen, can be prepared by reacting sulfamoylchromans of the formula II

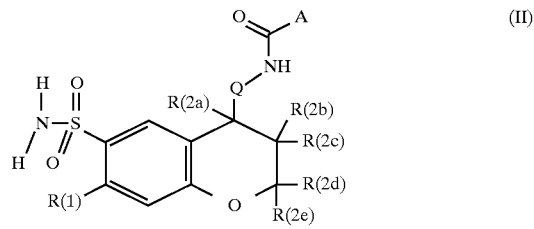

or their salts of the formula III

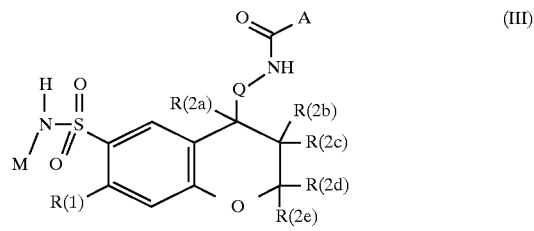

with R(3)-substituted isocyanates of the formula IV

to give substituted chromanylsulfonylureas of the formula Ia (where Z (in the formula I)=oxygen)

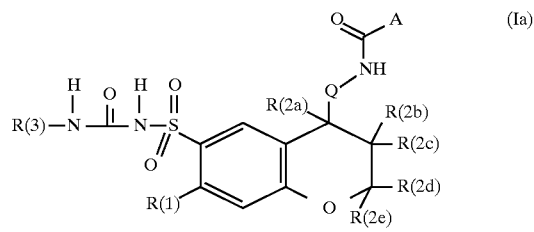

The radicals in the formulae II, III and IV here have the meanings indicated at the outset. Suitable cations M in the salts of the formula III here are, for example, alkali metal, alkaline earth metal, ammonium and tetraalkyl-ammonium ions. Equivalently to the R(3)-substituted isocyanates of the formula IV, it is possible to employ R(3)-substituted carbonic acid derivatives such as R(3)-substituted carbamic acid esters, R(3)-substituted carbamoyl halides or R(3)-substituted ureas.

b) Chromanylsulfonylureas of the formula I, in which R(3) is hydrogen and Z is oxygen, can be prepared by reaction of a sulfamoylchroman of the formula II or of its salt of the formula III with a trialkylsilyl isocyanate or silicon tetraisocyanate and cleavage (e.g. hydrolysis) of the primarily formed silicon-substituted chromanylsulfonylureas.

It is furthermore possible to convert a sulfamoylchroman of the formula II or its salt of the formula III into a chromanylsulfonylurea of the formula I in which R(3) is hydrogen and Z is oxygen by reaction with cyanogen halides and hydrolysis of the primarily formed N-cyanosulfonamides with mineral acids at temperatures of 0° C. to 100° C.

(c) A chromanylsulfonylurea of the formula Ia (where Z (in the formula I)=oxygen) can be prepared from a sulfamoylchroman of the formula II or its salt of the formula III using a trichloroacetamide of the formula V which is R(3)-substituted on the nitrogen,

in the presence of a base in an inert solvent according to Synthesis 1987, 734–735 at temperatures of 25° C. to 150° C.

Suitable bases are, for example, alkali metal or alkaline earth metal hydroxides, hydrides, amides or also alkoxides, such as sodium hydroxide, potassium hydroxide, calcium hydroxide, sodium hydride, potassium hydride, calcium hydride, sodium amide, potassium amide, sodium methoxide, sodium ethoxide, potassium methoxide or potassium ethoxide. Suitable inert solvents are ethers such as tetrahydrofuran, dioxane, ethylene glycol dimethyl ether, diglyme, ketones such as acetone or butanone, nitrites such as acetonitrile, nitro compounds such as nitromethane, esters such as ethyl acetate, amides such as dimethylformamide (DMF) or N-methylpyrrolidone (NMP), hexamethylphosphoric triamide, sulfoxides such as DMSO, sulfones such as sulfolane, hydrocarbons such as benzene, toluene, xylenes. Furthermore, mixtures of these solvents with one another are also suitable.

(d) A chromanylsulfonylthiourea of the formula Ib (where Z (in the formula I)=sulfur)

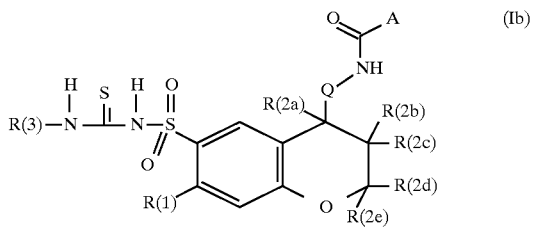

can be prepared from a sulfamoylchroman of the formula II or its salt of the formula III and an R(3)-substituted isothiocyanate of the formula VI

(e) A chromanylsulfonylthiourea of the formula I, in which R(3) is hydrogen and Z is sulfur, can be prepared by reaction of a sulfamoylchroman of the formula II or of its salt of the formula III with a trialkylsilyl isothiocyanate, e.g. trimethylsilyl isothiocyanate, or silicon tetraisothiocyanate and cleavage (e.g. hydrolysis) of the primarily formed silicon-substituted chromanylsulfonylthiourea. It is furthermore possible to react a sulfamoylchroman of the formula II or its salt of the formula III with benzoyl isothiocyanate and to react the intermediate benzoyl-substituted chromanylsulfonylthiourea with an aqueous mineral acid to give the compound of the formula Ib where R(3)=H. Similar processes are described in J. Med. Chem. 1992, 35, 1137–1144. A further variant consists in reacting the N-cyanosulfonamides mentioned in process (b) with hydrogen sulfide.

(f) A substituted chromanylsulfonylurea of the formula Ia can be prepared by a conversion reaction from a chromanylsulfonylthiourea of the formula Ib. The desulfurization, that is the replacement of the sulfur atom in the appropriately substituted chromanylsulfonylthiourea by an oxygen atom, can be carried out, for example, with the aid of oxides or salts of heavy metals or also by use of oxidants such as hydrogen peroxide, sodium peroxide or nitrous acid. A thiourea can also be desulfurized by treatment with chlorinating agents such as phosgene or phosphorus pentachloride. As intermediates, chloroformamidines or carbodiimides are obtained which, for example, can be converted into the corresponding substituted chromanylsulfonylureas by hydrolysis or addition of water.

(g) A chromanylsulfonylurea of the formula I in which Z is oxygen can be prepared from a chromanylsulfonyl halide, e.g. of the formula VII

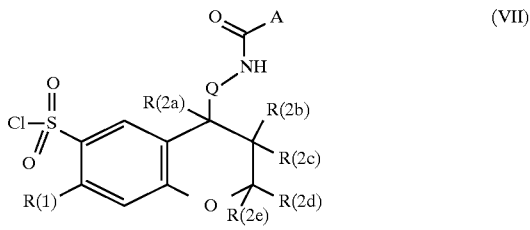

using an R(3)-substituted urea or an R(3)-substituted bis(trialkylsilyl)urea. Furthermore, the sulfonyl chloride of the formula VII can be reacted with parabanic acids to give a chromanylsulfonylparabanic acid, hydrolysis of which with mineral acids yields the corresponding chromanylsulfonylurea of the formula I (Z=O).

(h) A chromanylsulfonyl urea of the formula I in which Z is oxygen can be prepared by reaction of an amine of the formula R(3)—NH$_2$ with a chromanylsulfonyl isocyanate of the formula VIII

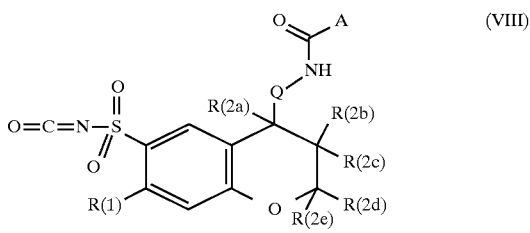

The sulfonyl isocyanate of the formula VIII can be obtained from the sulfamoylchroman of the formula II by customary methods, e.g. with phosgene, Just as with the isocyanate of the formula VIII, an amine R(3)—NH$_2$ can be reacted with a chromanylsulfonylcarbamic acid ester, a carbamoyl halide or a chromanylsulfonylurea of the formula Ia in which R(3) is hydrogen to give a compound of the formula I, in which Z is oxygen.

(i) A chromanylsulfonylthiourea of the formula I in which Z is sulfur can be prepared by reaction of an amine of the formula R(3)—NH$_2$ with chromanylsulfonyl isothiocyanate of the formula IX

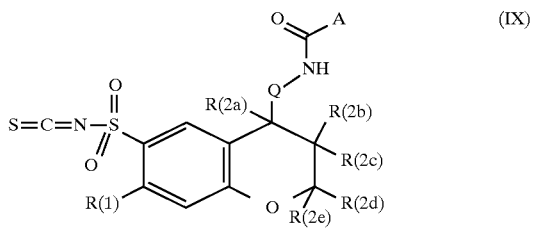

Likewise, an amine R(3)—NH$_2$ can be reacted with a chromanylsulfonylcarbamic acid thioester or a -carbamoyl thiohalide to give a compound of the formula I in which Z is sulfur.

The sulfonyl isothiocyanates of the formula IX can be prepared by reaction of a corresponding sulfonamide with alkali metal hydroxide and carbon disulfide in an organic solvent, such as DMF, DMSO or N-methylpyrrolidone. The di-alkali metal salt of the sulfonyldithiocarbamic acid thus obtained can be reacted in an inert solvent with a slight excess of phosgene or of a phosgene substitute such as triphosgene, with a chloroformic acid ester (2 equivalents) or with thionyl chloride. The solution of the sulfonyl isothiocyanate thus obtained can be reacted directly with the corresponding amines or ammonia.

(j) An appropriately substituted chromanylsulfonyl- or -sulfonylurea can be oxidized using an oxidant, such as hydrogen peroxide, sodium peroxide or nitrous acid, to give the chromanylsulfonylurea of the formula I in which Z is oxygen.

The starting compounds for the processes mentioned for the synthesis of the chromanylsulfonylureas of the formula I are prepared by methods known per se, such as are described in the literature (for example in the standard works such as Houben-Weyl, Methoden der Organischen Chemie [Methods of Organic Chemistry], Georg Thieme Verlag, Stuttgart;

Organic Reactions, John Wiley & Sons, Inc., New York; and in the patent applications indicated above), expediently under reaction conditions which are known and suitable for the reactions mentioned. In this case use can be made of variants which are known per se, but not mentioned here in greater detail. If desired, the starting substances can also be formed in situ in such a way that they are not isolated from the reaction mixture, but immediately reacted further.

4-Aminoalkylchromans are described, for example, in European Offenlegungsschrift EP-A-325 964 and U.S. Pat. No. 5,140,039 or 5,185,364 or can be prepared by the methods indicated there. Suitably substituted amines of the formula XI can be acylated as indicated in Scheme 1 to give the amides of the formula XII and then subjected to halo-sulfonation. Suitable acylating agents for amino groups are expediently the alkyl esters, halides (for example chlorides or bromides) or anhydrides of carboxylic acids of the formula

R(5)COY.

R(5) in this connection is a trihalomethyl radical or a (C$_1$–C$_4$)-alkyl radical, or R(5)COY is a benzoic acid derivative of the formula ACOY, where A here in accordance with the meaning of this radical mentioned at the outset is substituted or unsubstituted phenyl. Y is a leaving group such as halide, (C$_1$–C$_4$)-alkoxy, trihaloacetate or (C$_1$–C$_4$)-carboxylate.

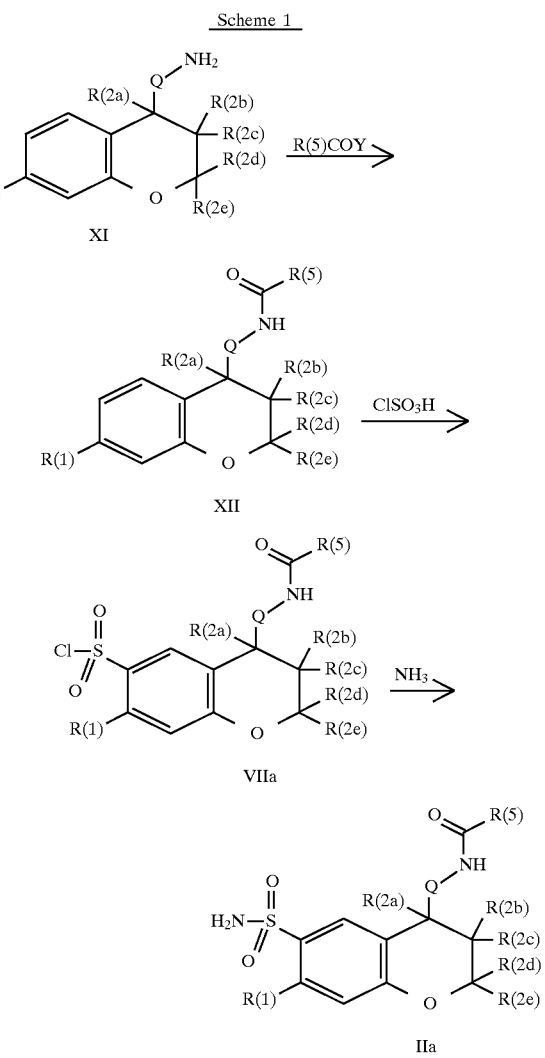

The syntheses of the compounds of the formula XII are customarily carried out with addition of a tertiary base such as, for example, pyridine or a trialkylamine in the presence or absence of an inert solvent, it also being possible for a catalyst such as, for example, dimethylaminopyridine to be present. The reaction can be achieved at temperatures from approximately 0° C. to 160° C., preferably from 20° C. to 150° C. The acyl group of the compounds of the formula XII can be either a protective group, or, in the case of the benzoic acid derivatives, i.e. if R(5) is A with the meaning of A explained above, part of the compound of the formula I. Suitable inert solvents are ethers such as tetrahydrofuran, dioxane, glycol ethers such as ethylene glycol monomethyl or monoethyl ether (methyl glycol or ethyl glycol), ethylene glycol dimethyl ether, diglyme, ketones such as acetone or butanone, nitriles such as acetonitrile, amides such as dimethylformamide (DMF) or N-methylpyrrolidone (NMP), hexamethylphosphoric triamide, sulfoxides such as DMSO, chlorinated hydrocarbons such as dichloromethane, chloroform, trichloroethylene, 1,2-dichloroethane or carbon tetrachloride, hydrocarbons such as benzene, toluene or xylenes. Furthermore, mixtures of these solvents with one another are also suitable.

If in the compounds of the formula I the group A is the radical of the formula

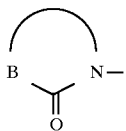

with the definition of B stipulated at the outset, or B is a radical of the formula

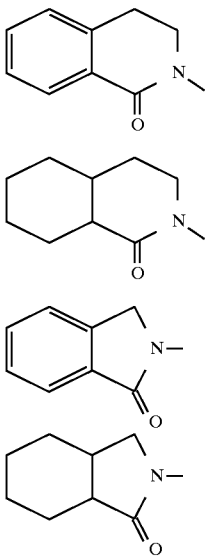

then the acylated amines corresponding to the formula XII can be prepared as follows:

The amine of the formula XI is first converted into an isocyanate or a reactive carbonic acid derivative. The conversion of the amine XI into an isocyanate (Scheme 2) can be carried out in a known manner by reaction of XI with Scheme 2

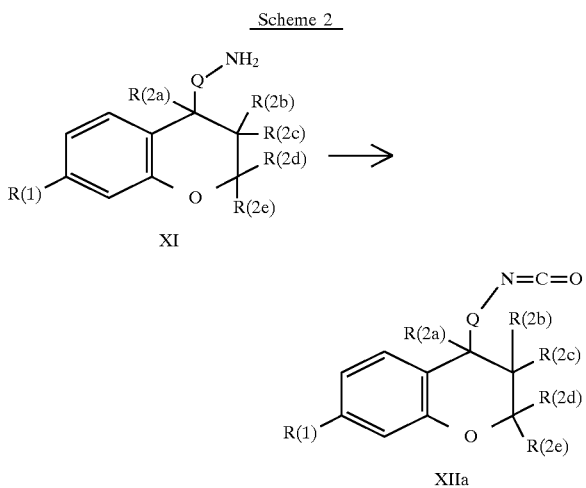

carbonyl halides such as phosgene or triphosgene in the presence of tertiary alkylamines or pyridine and inert solvents. Suitable inert solvents are ethers such as tetrahydrofuran, dioxane, ethylene glycol dimethyl ether, diglyme, ketones such as acetone or butanone, nitriles such as acetonitrile, nitro compounds such as nitromethane, esters such as ethyl acetate, amides such as dimethylformamide (DMF) or N-methylpyrrolidone (NMP), hexamethylphosphoric triamide, sulfoxides such as DMSO, sulfones such as sulfolane, hydrocarbons such as benzene, toluene or xylenes. Furthermore, mixtures of these solvents with one another are also suitable. Suitable reactive carbonic acid derivatives are carbonic acid esters, such as can be synthesized from alkyl chloroformates and XI and suitable tertiary alkylamines or pyridine. Furthermore N,N'-carbonyldiimidazole and analogous reactive derivatives can be employed as isocyanate equivalents (Staab, H. A., Synthesen mit heterocyclischen Amiden (Azoliden) [Syntheses with heterocyclic amides (azolides)], Angewandte Chemie 74 (1962), No. 12, pp. 407–423).

The isocyanate of the formula XIIa or corresponding urethanes can then be coupled, for the introduction of the second molecular component, to a compound of the formula

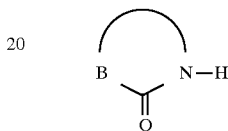

with the meaning of B mentioned at the outset or a compound of the formula

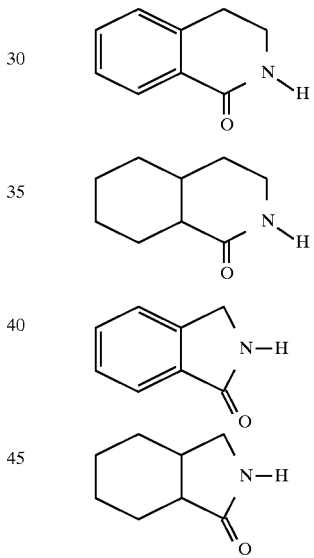

in the presence or absence of inert solvents at temperatures of, for example, 100°–170° C. (Justus Liebigs Ann. Chem. 1956, 598, p. 203) and yield the acylurea derivatives of the formula XIIb corresponding to the formula XII, in which A is the heterocyclic radicals mentioned at the outset (Scheme 3).

Scheme 3

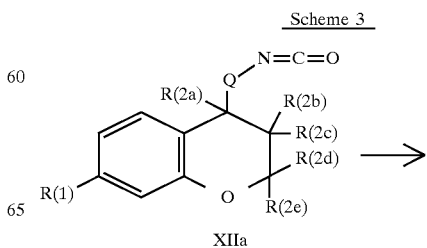

-continued
Scheme 3

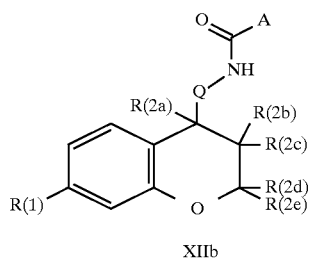

XIIb

The acylated amines of the formulae XII and XIIb obtained according to Scheme 1 or 2/3 can be converted in a known manner into the sulfonamides of the formula II. The sulfonamides of the formula II are prepared by methods known per se and namely under reaction conditions which are known and suitable for the reactions mentioned. In this case, use can also be made of variants which are known per se, but not mentioned here in greater detail. If desired, the syntheses can be accomplished in one, two or more steps. In particular, processes are preferred in which the acylated amine of the formula XII or XIIb is converted by electrophilic reagents in the absence or presence of inert solvents at temperatures from −10° C. to 120° C., preferably from 0° C. to 100° C., into aromatic sulfonic acids or their derivatives, such as, for example, sulfonyl halides. For example, sulfonations can be carried out with sulfuric acids or oleum, or halosulfonations can be carried out with halosulfonic acids, reaction with sulfuryl halides in the presence of anhydrous metal halides or reaction with thionyl halides in the presence of anhydrous metal halides with subsequent oxidation carried out in a known manner to give sulfonyl chlorides. If sulfonic acids are the primary reaction products, these can be converted into the sulfonyl halides in a known manner by acid halides such as, for example, phosphorus trihalides, phosphorus pentahalides, phosphorus oxychlorides, thionyl halides or oxalyl halides, either directly or by treatment with tertiary amines, such as, for example, pyridine or trialkylamines, or with alkali metal or alkaline earth metal hydroxides or reagents which form these basic compounds in situ. The sulfonic acid derivatives are converted into sulfonamides in a manner known from the literature, preferably sulfonyl chlorides are reacted with aqueous ammonia in inert solvents at temperatures from 0° C. to 100° C. Furthermore, sulfonamides can be synthesized by processes described in the literature from the acylated amines of the formula XII prepared according to Scheme 1 by reactions with alkali metal or alkaline earth metal organometallic reagents in inert solvents and under an inert gas atmosphere at temperatures from −100° C. to 50° C., preferably from −100° C. to 30° C., reaction with sulfur dioxide and subsequent thermal treatment with amidosulfonic acid.

If the acyl group R(5)CO functions as a protective group for the amino group in the compound of the formula XI, this can be removed with acids or bases after preparation of the sulfonamide of the formula IIa. By cleavage with aqueous acids or acids in inert solvents the corresponding acid addition salt may be formed. For example, sulfuric acid, hydrohalic acids, such as hydrochloric acid or hydrobromic acid, phosphoric acids such as orthophosphoric acid or polyphosphoric acid or other customary acids with which amides can be cleaved are suitable for this reaction. The cleavage of the acylated amine of the formula XII with bases can also be carried out in aqueous or inert solvents. Suitable bases are, for example, alkali metal or alkaline earth metal hydroxides or also alkoxides, such as sodium hydroxide, potassium hydroxide, calcium hydroxide, sodium hydride, sodium methoxide, sodium ethoxide, potassium methoxide or potassium ethoxide.

From the sulfonamide-substituted amines prepared in this way or their acid addition compounds, the sulfamoylchromans of the formula II in which the nitrogen atom carries the acyl group ACO can be prepared as mentioned above. Depending on the nature of the members R(1), R(2a), R(2b), R(2c), R(2d), R(2e), R(3), Z, Q and A, in isolated cases one or other of the processes mentioned for the preparation of the compounds of the formula I will be unsuitable or at least make necessary precautions for the protection of reactive groups. Comparatively rarely occurring cases of this type can be recognised without difficulty by the person skilled in the art, and it presents no difficulties in such cases to successfully use another of the synthetic routes described.

The compounds of the formula I can have one or more chiral centers. If one or more chiral centers are present, compounds of the formula I having uniform stereochemistry at these centers are preferred. Compounds of the formula I having one or more chiral centers can be obtained on preparation thereof as racemates or, if optically active starting substances are used, also in optically active form. If the compounds have two or more chiral centers, then they can be obtained on synthesis as mixtures of racemates from which the individual isomers can be isolated in pure form, for example by recrystallizing from inert solvents. If desired, racemates which are obtained can be separated into their enantiomers mechanically or chemically by methods known per se. Thus diastereomers can be formed from the racemate by reaction with an optically active resolving agent. Suitable resolving agents for basic compounds are, for example, optically active acids, such as the R- or R,R- and S- or S,S-forms of tartaric acid, dibenzoyltartaric acid, diacetyltartaric acid, camphorsulfonic acid, mandelic acid, malic acid or lactic acid. The various forms of the diastereomers can be separated in a manner known per se, for example by fractional crystallization, and the enantiomers of the formula I can be set free from the diastereomers in a manner known per se. Enantiomeric separations are furthermore carried out by chromatography on optically active support materials. A particularly simple process for the preparation of optically uniform compounds consists, for example, in resolving the amines of the formula XI into the enantiomers by recrystallization with optically active acids such as, for example, (+)- or (−)-mandelic acid and then converting as described above into the final compounds of the formula I which, for their part, are now enantiomerically pure.

The compounds of the formula I and their physiologically acceptable salts are useful therapeutics which are not only suitable as antiarrhythmics, but also for treatment and prophylaxis in disorders of the cardiovascular system, cardiac insufficiency, heart transplants or cerebral vascular disorders in humans or mammals (for example monkeys, dogs, mice, rats, rabbits, guinea-pigs, cats and larger productive animals e.g. cattle and pigs). Physiologically acceptable salts of the compounds of the formula I are understood according to Remmington's Pharmaceutical Science, 17th Edition, 1985, pages 14–18, for example, as meaning compounds of the formula X,

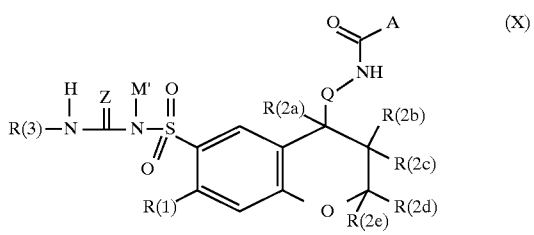

which can be prepared from nontoxic organic and inorganic bases and chromanylsulfonyl(thio)ureas of the formula I. Preferred salts in this context are those in which the cation M' in the formula X is a sodium, potassium, rubidium, calcium, magnesium or ammonium ion or an ammonium ion having organic radicals, and also the acid addition products of compounds of the formula I and basic amino acids, such as, for example, lysine or arginine. The salts can be obtained according to the customary procedure, for example by reaction of the compounds of the formula I with suitable bases, such as, for example, sodium or potassium hydroxide or an amine, in a solvent or diluent. Suitable physiologically acceptable salts in the case of compounds of the formula I having basic groups are furthermore the addition products with nontoxic inorganic and organic acids which can likewise be obtained, for example, by combining the components in a suitable solvent or diluent. Suitable acids are, for example, sulfuric acid, hydrohalic acids, such as hydrochloric or acid hydrobromic acid, phosphoric acids such as orthophosphoric acid or polyphosphoric acid, sulfamic acid, furthermore organic acids, in particular aliphatic, alicyclic, araliphatic, aromatic or heterocyclic mono- or polybasic carboxylic, sulfonic or sulfuric acids, for example acetic acid, propionic acid, pivalic acid, diethylacetic acid, malonic acid. succinic acid, pimelic acid, fumaric acid, maleic acid, lactic acid, tartaric acid, malic acid, benzoic acid, salicylic acid, 2- or 3-phenylpropionic acid, phenylacetic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalenemono- and -disulfonic acids or laurylsulfuric acid.

The compounds of the present invention are particularly useful pharmaceuticals for the treatment of cardiac arrhythmias of all sorts of origins and for the prevention of sudden heart death due to arrhythmia and can therefore be used as antiarrhythmics. Examples of arrhythmic disorders of the heart are supraventricular arrhythmias such as, for example, atrial tachycardias, atrial flutters or paroxysmal supraventricular arrhythmias, or ventricular arrhythmias such as ventricular extrasystoles, but in particular life-threatening ventricular tachycardias or the particularly dangerous ventricular fibrillation. They are particularly suitable in those cases where arrhythmias are the result of a constriction of a coronary vessel, such as occur, for example, in angina pectoris or during an acute cardiac infarct or as a chronic result of a cardiac infarct. They are therefore particularly suitable for the prevention of sudden heart death in postinfarct patients.

Further clinical syndromes where arrhythmias of this type and/or sudden heart death due to arrhythmia play a part are, for example, cardiac insufficiency or cardiac hypertrophy as a result of a chronically raised blood pressure.

Moreover, the compounds of the present invention are able to positively affect decreased contractility of the heart. What is concerned here can be a disease-related decrease in cardiac contractility, such as, for example, in cardiac insufficiency, but also acute cases such as heart failure as a result of the effects of shock. Likewise, in the case of a heart transplant, the heart can recover its functional capacity more rapidly and reliably after operation has taken place. The same applies to operations on the heart which make necessary a temporary stopping of cardiac activity by means of cardioplegic solutions.

The compounds of the formula I according to the invention and their physiologically acceptable salts can be used for the production of pharmaceutical preparations. In this connection, they can be brought into a suitable dose form together with at least one solid or liquid excipient or auxiliary on their own or in combination with other pharmaceuticals, e.g. pharmaceuticals having cardiovascular activity such as, for example, calcium antagonists or ACE inhibitors. Pharmaceutical preparations and pharmaceuticals which contain an efficacious amount of one or more compounds of the formula I or their physiologically acceptable salts, the use of the compounds for the production of pharmaceuticals and processes for the production of such pharmaceuticals are likewise a subject of the present invention. These preparations can be used as pharmaceuticals in human or veterinary medicine.

Possible excipients are organic or inorganic substances which are suitable for enteral (for example oral) or parenteral (for example intravenous) administration or for topical application and do not react with the compounds of the formula I, for example water, vegetable oils, alcohols such as ethanol, propanediol or benzyl alcohols, polyethylene glycols, polypropylene glycols, glycerol triacetate, gelatin, carbohydrates, such as lactose or starch, magnesium stearate, talc, lanolin or petroleum jelly. In particular, pharmaceutical forms such as tablets, coated tablets, capsules, suppositories, solutions, preferably oily or aqueous solutions, syrups, juices or drops and furthermore suspensions or emulsions are used for oral and rectal administration, ointments, creams, pastes, lotions, gels, sprays, foams, aerosols, solutions (for example in alcohols, such as ethanol, isopropanol or 1,2-propanediol or mixtures thereof with one another or with water) or powders are used for topical application. Further suitable pharmaceutical forms are also, for example, implants. The compounds of the formula I can also be lyophilized and the lyophilizates obtained used, for example, for the preparation of injection preparations. In particular, liposomal preparations are also suitable for topical application. The pharmaceutical preparations can contain auxiliaries such as lubricants, preservatives, stabilizers and/or wetting agents, emulsifiers, salts (e.g. for affecting the osmotic pressure), buffer substances, colorants and flavorings and/or aromatizers. If desired, they can also contain one or more further active compounds, for example one or more vitamins.

The doses which are necessary for the treatment of cardiac arrhythmias using the compounds of the formula I depend on whether the therapy is acute or prophylactic, and depend on the particular individual case. Normally, a dose range from approximately at least 0.01, preferably 0.1 mg, in particular 1 mg to at most 100 mg, preferably 10 mg per kg per day is adequate if prophylactic treatment is carried out. A dose range from 1 to 10 mg per kg per day is particularly suitable, The dose can be administered in this case in the form of an oral or parenteral individual dose or divided into several, in particular, for example, up to four, individual doses. If acute cases of cardiac arrhythmias are treated, for example in an intensive care unit, parenteral administration, for example by injection or infusion, may be advantageous. A preferred dose range in critical situations can be 10 to 100 mg and can be administered, for example, as an intravenous continuous infusion.

According to the invention, apart from the compounds described in the working examples, the compounds of the formula I compiled in the following table, for example, can also be obtained:

4-(5-chloro-2-methoxybenzamidomethyl)-6-(methylaminocarbonylaminosulfonyl)-7-ethylchroman 4-(5-bromo-2-methoxybenzamidomethyl)-6-(methylaminocarbonylaminosulfonyl)-7-ethylchroman 4-(5-bromo-2-methoxybenzamidomethyl)-6-(methylaminothiocarbonylaminosulfonyl)-7-methoxychroman 4-(5-chloro-2-methoxybenzamidoethyl)-6-(methylaminocarbonylaminosulfonyl)-7-ethylchroman 4-(5-chloro-2-methoxybenzamidoethyl)-6-(methylaminothiocarbonylaminosulfonyl)-7-methoxychroman 4-(5-bromo-2-methoxybenzamidoethyl)-6-(methylaminocarbonylaminosulfonyl)-7-ethylchroman 4-(5-bromo-2-methoxybenzamidoethyl)-6-(methylaminothiocarbonylaminosulfonyl)-7-methoxychroman 4-(5-chloro-2-methoxybenzamidoethyl)-6-(methylaminocarbonylaminosulfonyl)-7-methoxychroman 4-(5-chloro-2-methoxybenzamidoethyl)-6-(methylaminothiocarbonylaminosulfonyl )-7-ethoxychroman 4-(5-chloro-2-methoxybenzamidomethyl)-6-(ethylaminocarbonylaminosulfonyl)-7-ethylchroman 4-(5-bromo-2-methoxybenzamidomethyl)-6-(ethyiaminocarbonylaminosulfonyl)-7-ethylchroman 4-(5-bromo-2-methoxybenzamidomethyl)6-(ethylaminothiocarbonylaminosulfonyl )-7-methoxychroman 4-(5-chloro-2-methoxybenzamidoethyl)-(ethylaminocarbonylaminosulfonyl)-7-ethylchroman 4-(5-chloro-2-methoxybenzamidoethyl)-6-(ethylaminothiocarbonylaminosulfonyl)-7-methoxychroman 4-(5-bromo-2-methoxybenzamidoethyl)4-(ethylaminocarbonylaminosulfonyl)-7-ethylchroman 4-(5-bromo-2-methoxybenzamidoethyl!)-6-(ethylaminothiocarbonylaminosulfonyl)-7-methoxychroman 4-(5-chloro-2-methoxybenzamidoethyl)6-(ethylaminocarbonylaminosulfonyl)-7-methoxychroman 4-(5-chloro-2-methoxybenzamidoethyl)-6-(ethylaminothiocarbonylaminosulfonyl )-7-ethoxychroman 4-(5-fluoro-2-methoxybenzamidomethyl)-6-(ethylaminocarbonylaminosulfonyl )-7-methoxychroman 4-(5-fluoro-2-methoxybenzamidomethyl)-6-(methylaminocarbonylaminosulfonyl)-7-methylchroman 4-(5-fluoro-2-methoxybenzamidomethyl)-6-(methylaminothiocarbonylaminosulfonyl )-7-methylchroman 4-(5-fluoro-2-methoxybenzamidomethyl)-6-(methylaminocarbonylaminosulfonyl )-7-ethylchroman 4-(5-fluoro-2-methoxybenzamidomethyl )-6-(methylaminothiocarbonylaminosulfonyl)-7-ethylchroman 4-(5-fluoro-2-methoxybenzamidomethyl)-6-(methylaminocarbonylaminosulfonyl)-7-ethoxychroman 4-(5-fluoro-2-methoxybenzamidomethyl )-6-(methylaminothiocarbonylaminosulfonyl )-7-ethoxychroman 4-(5-fluoro-2-methoxybenzamidomethyl)-6-(ethylaminocarbonylamino-sulfonyl)-7-ethoxychroman 4-(5-fluoro-2-methoxybenzamidomethyl)-6-(ethylaminothiocarbonylamino-sulfonyl )-7-ethoxychroman 4((3-ethyl-4-methyl-2-oxo-3-pyrroline-1-carboxamido)ethyl)-6-(methylaminothiocarbonylaminosulfonyl)-7-ethoxychroman 4-((3-ethyl-4-methyl-2-oxo-3-pyrroline-1 -carboxamido)ethyl)-4-(methyl aminocarbonylaminosulfonyl)-7-ethoxychroman 4-((3-ethyl-4-methyl-2-oxo-3-pyrroline-1 -carboxamido)ethyl)-6-(methylaminothiocarbonylaminosulfonyl)-7-ethylchroman 4-((3-ethyl-4-methyl-2-oxo-3-pyrroline-1 -carboxamido)ethyl)-6-(methylamino-carbonylamino-sulfonyl)-7-ethylchroman 4-((2-oxo-3-pyrroline-1-carboxamido)ethyl)-6-(methylaminothiocarbonylaminosulfonyl)-7-ethoxychroman 4-((2-oxo-3-pyrroline-1-carboxamido)ethyl)-6-(methylaminocarbonylaminosulfonyl)-7-ethoxychroman 4-((2-oxo-3-pyrroline-1-carboxamido)ethyl )-6-(methylaminothiocarbonylaminosulfonyl)-7-ethylchroman 4-((2-oxo-3-pyrroline-1-carboxamido)ethyl)-6-(methylaminocarbonylamino-sulfonyl)-7-ethylchroman 4-((2-oxo-3-pyrroline-1-carboxamido)ethyl)-6-(methylaminothiocarbonylaminosulfonyl)-7-ethoxychroman 4-((2-oxo-3-pyrroline-1-carboxamido)ethyl)-6-(methylaminocarbonylaminosulfonyl)-7 -ethoxychroman

EXAMPLE 1

4-(5-Chloro-2-methoxybenzamidomethyl)-6-(methylaminocarbonylaminosulfonyl)-7-methoxychroman

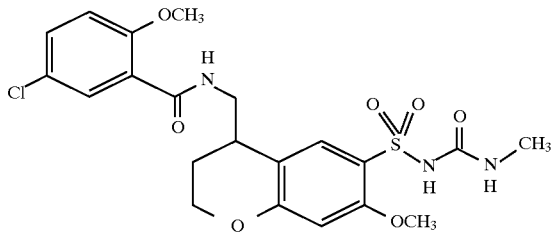

1.76 g (4 mmol) of 4-(5-chloro-2-methoxybenzamidomethyl)-6-sulfamoyl-7-methoxychroman are dissolved in 10 ml of dry DMSO and, after addition of 0.4 g (10 mmol) of pulverized sodium hydroxide and 1.05 g (6 mmol) of N-methyltrichloroacetamide, the mixture is heated at 80° C. for 30 minutes. The cooled reaction mixture is introduced into ice water, clarified with activated carbon and acidified to pH 1. The precipitate is filtered off with suction, dried and recrystallized twice from ethanol/DMF. 4-(5-Chloro-2-methoxy benzamidomethyl)-6-(methylaminocarbonylaminosulfonyl)-7-methoxychroman melts at 207° C.

Preparation of the starting compound 4-(5-chloro-2-methoxy-benzamidomethyl)-6-sulfamoyl-7-methoxychroman 14.8 g (64.4 mmol) of 4-aminomethyl-7-methoxychroman hydrochloride are dissolved in 75 ml of pyridine and treated with cooling to 0° C. with 13.4 g of 2-methoxy-5-chlorobenzoyl chloride. The mixture is stirred for 1.5 hours at room temperature and for 1 hour at 60° C. The cooled reaction mixture is partitioned between water and methylene chloride. The aqueous phase is extracted three times with methylene chloride. The combined organic phases are washed with 2N hydrochloric acid, water and bicarbonate solution. After drying and evaporating the organic phase, an oil is obtained. 20 g of this oil are cooled to −20° C. 30 ml of precooled chlorosulfonic acid are added with stirring. The mixture is allowed to come to room temperature with shaking and a further 5 ml of chlorosulfonic acid are added. After stirring into ice water, the precipitate obtained is filtered off with suction and, after washing with a little cold water, introduced into a solution of 200 ml of acetone and 120 ml of concentrated ammonia cooled to −20° C. The mixture is allowed to warm to room temperature, and after standing overnight the solution is concentrated in vacuo. The residue is treated with concentrated hydrochloric acid with ice cooling. The precipitate obtained is filtered off with suction and recrystallized from glacial acetic acid/methanol. 4-(5-Chloro-2-methoxybenzamidomethyl)-6-sulfamoyl-7-methoxychroman is obtained in the form of colorless crystals of melting point 202° C.

EXAMPLE 2

4-(5-Chloro-2-methoxybenzamidomethyl)-6-(ethylaminocarbonyl-aminosulfonyl)-7-methoxychroman

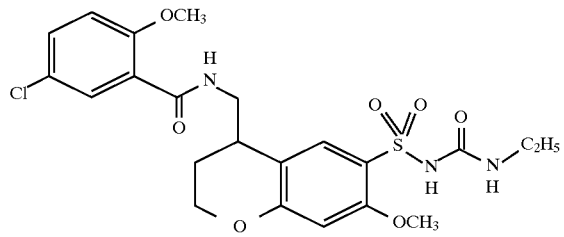

4-(5-Chloro-2-methoxybenzamidomethyl)-6-(ethylaminocarbonyl-aminosulfonyl)-7-methoxychroman is synthesized analogously to Example 1 from 4-(5-chloro-2-methoxybenzamidomethyl)-6-sulfamoyl-7-methoxychroman and N-ethyltrichloroacetamide. Melting point: 211°–213° C.

EXAMPLE 3

4-(5-Chloro-2-methoxybenzamidomethyl)-6-(n-propylaminocarbonyl-aminosulfonyl)-7-methoxychroman

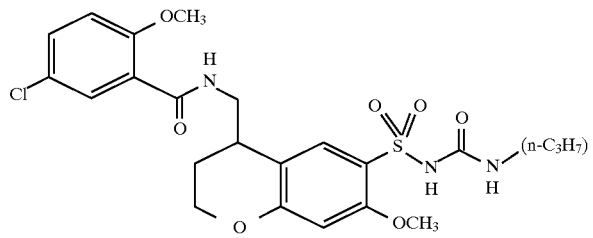

4-(5-Chloro-2-methoxybenzamidomethyl)-6-(n-propylaminocarbonylaminosulfonyl)-7methoxychroman is prepared analogously to Example 1 from 4-(5Chloro-2-methoxybenzamidomethyl)-6-sulfamoyl-7-methoxychroman and N-(n-propyl)trichloroacetamide. Melting point: 159°–160° C.

EXAMPLE 4

4-(5-Chloro-2-methoxybenzamidomethyl)-6-(methylaminothiocarbonylaminosulfonyl)-7-methoxychroman

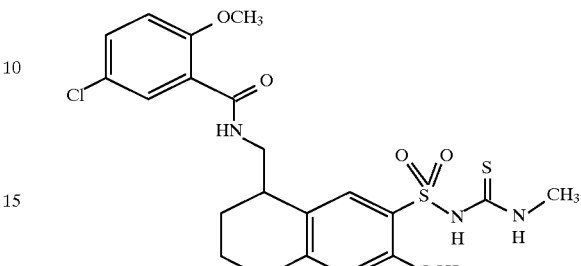

1.76 g (4 mmol) of 4-(5-chloro-2-methoxybenzamidomethyl6-sulfamoyl-7-methoxychroman from Example 1 are dissolved in 5 ml of dry DMF and treated with 1.65 g of potassium carbonate and with 0.35 g (4.8 mmol) of methyl isothiocyanate. After stirring at 80° C. for one hour, the mixture is cooled and introduced into ice water, clarified with carbon and acidified to pH 1. The precipitate is filtered off with suction, dried and recrystallized from ethanol/DMF. Melting point 121° C.

EXAMPLE 5

4-(5-Chloro-2-methoxybenzamidomethyl)-6-(ethylaminothiocarbonylaminosulfonyl)-7-methoxychroman

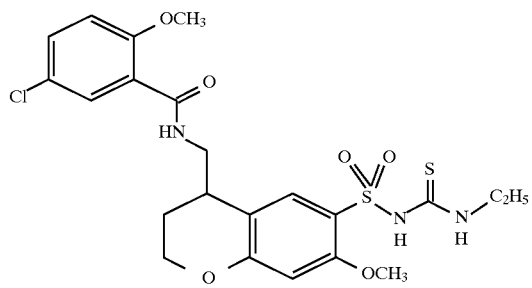

4-(5-Chloro-2-methoxybenzamidomethyl)-6-(ethylaminothiocarbonylaminosulfonyl)-7-methoxychroman is synthesize as described in Example 4 from 4-(5-chloro-2-methoxybenzamidomethyl)-6-sulfamoyl-7-methoxychroman and ethyl isothiocyanate. Melting point: 196°–197° C.

EXAMPLE 6

4-(5-Chloro-2-methoxybenzamidomethyl)-6-(n-propylaminothiocarbonylaminosulfonyl)-7-methoxychroman

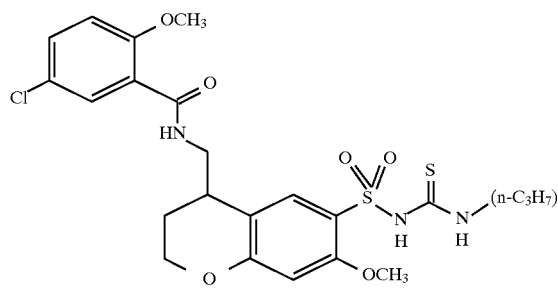

4-(5-Chloro-2-methoxybenzamidomethyl)-6-(n-propylaminothiocarbonylaminosulfonyl)-7-methoxychroman is prepare from 4-(5-chloro-2-methoxybenzamidomethyl)-6-sulfamoyl-7-methoxychroman and n-propyl isothiocyanate. Melting point: 183°–184° C.

EXAMPLE 7
4-(5-Chloro-2-methoxybenzamidomethyl)-6-(isopropylaminothiocarbonylaminosulfonyl)-7-methoxychroman

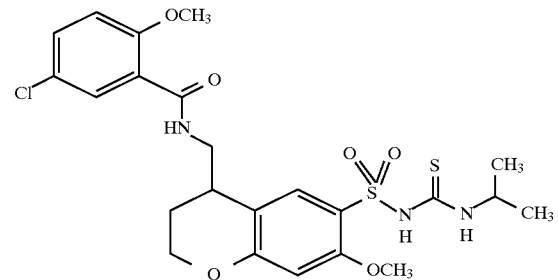

4-(5-Chloro-2-methoxybenzamidomethyl)-6-(isopropylaminothiocarbonylaminosulfonyl)-7-methoxychroman is synthe from 4-(5-chloro-2-methoxybenzamidomethyl )-6-sulfamoyl-7-methoxychroman and isopropyl isothiocyanate. Melting point: 184°–185° C.

EXAMPLE 8
4-(5-Chloro-2-methoxybenzamidomethyl)-6-(n-butylaminothiocarbonylaminosulfonyl)-7-methoxychroman

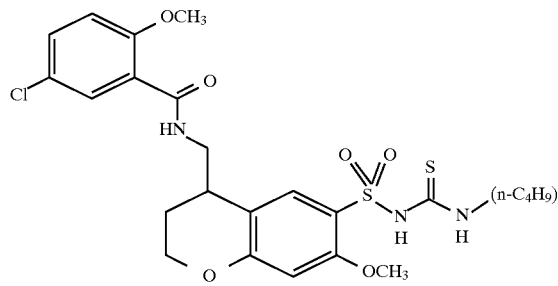

4-(5-Chloro-2-methoxybenzamidomethyl)-6-(n-butylaminothiocarbonylaminosulfonyl)-7-methoxychroman is prepared analogously to Example 4 from 4-(5-chloro-2-methoxybenzamidomethyl)-6-sulfamoyl-7-methoxychroman and n-butyl isothiocyanate. Melting point: 167° C.

EXAMPLE 9
4-(5-Chloro-2-methoxybenzamidomethyl)-6-(methylaminocarbonylaminosulfonyl)-7-ethoxychroman

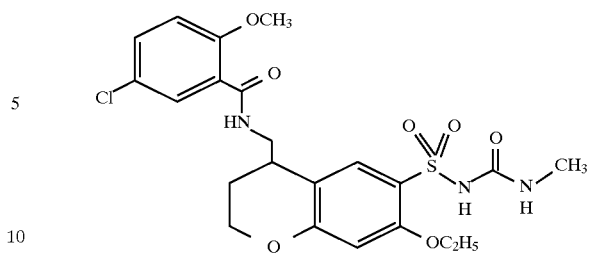

4-(5-Chloro-2-methoxy-benzamidomethyl)-6-(methylaminocarbonylaminosulfonyl)-7ethoxychroman is prepared as described in Example 1 from 4-(5-Chloro-2-methoxybenzamidomethyl)6-sulfamoyl-7-ethoxy-chroman and N-methyltrichloroacetamide. Melting point: 207°–208° C.

Preparation of the starting compound 4-(5-chloro-2-methoxy-benzamido-methyl)-6-sulfamoyl-7-ethoxychroman

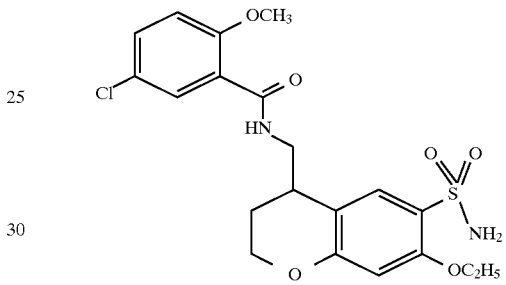

4-(5-Chloro-2-methoxybenzamidomethyl)-6-sulfamoyl-7-ethoxychroman is prepared analogously to the starting compound described in Example 1, starting from 4-aminomethyl-7-ethoxychroman and 5-chloro-2-methoxybenzoyl chloride. The intermediate formed in this way is subsequently reacted with chlorosulfonic acid and then ammonia. 4-(5-Chloro-2-methoxybenzamidomethyl) 6-sulfamoyl-7-ethoxychroman is obtained. Melting point: 204°–205° C.

EXAMPLE 10
4-(5-Chloro-2-methoxy-benzamidomethyl)-6-(methylaminothiocarbonylaminosulfonyl)-7-ethoxychroman

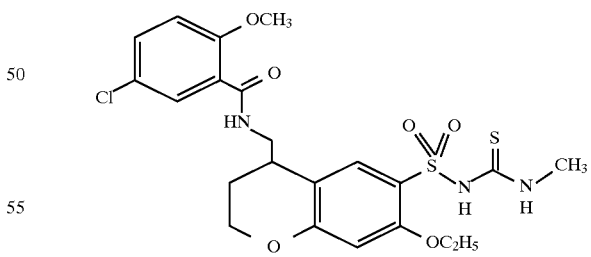

4-(5-Chloro-2-methoxy-benzamidomethyl)-6-(methylaminothiocarbonylaminosulfonyl)-7-ethoxychroman is prepared as described in Example 4 from 4-(5-chloro-2-methoxybenzamidomethyl)-6-sulfamoyl-7-ethoxychroman and methyl isothiocyanate. Melting point: 202° C.

EXAMPLE 11
4-(5-Fluoro-2-methoxybenzamidomethyl)-6-(methylaminocarbonylaminosulfonyl)-7-methoxychroman

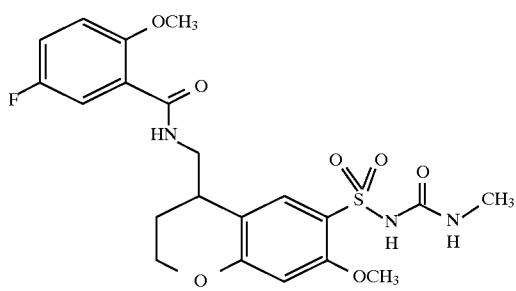

4-(5-Fluoro-2-methoxy-benzamidomethyl)-6-(methylaminocarbonylaminosulfonyl)-7-methoxychroman is synthesized analogously to Example 1 from 4-(5-fluoro-2-methoxybenzamidomethyl)-6-sulfamoyl-7-methoxychroman and N-methyltrichloroacetamide. Melting point: 193°–194° C.

Preparation of the starting compound 4-(5-fluoro-2-methoxybenzamidomethyl)-6-sulfamoyl-7-methoxychroman

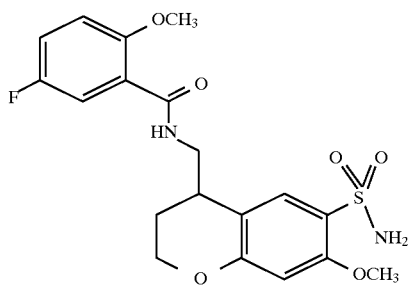

4-(5-Fluoro-2-methoxybenzamidomethyl)-6-sulfamoyl-7-methoxychroman is prepared analogously to Example 1, starting from 4-aminomethyl-7-methoxychroman and 2-methoxy-5-fluorobenzoic acid. The intermediate is sulfochlorinated—as described in Example 1—and subsequently reacted with ammonia to give the corresponding sulfamoyl compound. Melting point: 206° C.

EXAMPLE 12

4-(5-Fluoro-2-methoxybenzamidomethyl)-6-(methylaminothiocarbonylaminosulfonyl)-7-methoxychroman

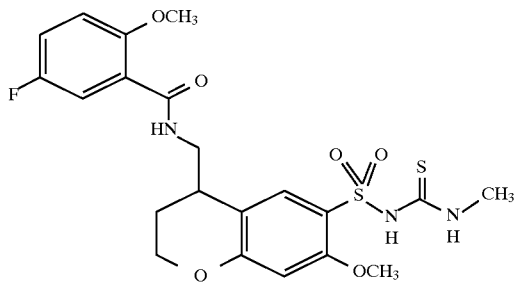

4-(5-Fluoro-2-methoxybenzamidomethyl)-6-(methylaminothiocarbonylaminosulfonyl)-7-methoxychroman is obtained analogously to Example 4 by reaction of 4-(5-fluoro-2-methoxybenzamidomethyl)-6-sulfamoyl-7-methoxychroman and methyl isothiocyanate. Melting point: 194° C.

EXAMPLE 13

4-(5-Fluoro-2-methoxybenzamidomethyl)-6-(ethylaminothiocarbonylaminosulfonyl)-7-methoxychroman

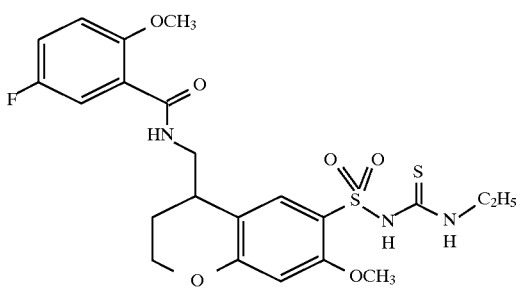

4-(5-Fluoro-2-methoxybenzamidomethyl)-6-(ethylaminothiocarbonylaminosulfonyl)-7-methoxychroman is obtained as described in Example 4 from 4-(5-fluoro-2-methoxy-benzamidomethyl)-6-sulfamoyl-7-methoxychroman and ethyl isothiocyanate. Melting point: 207° C.

EXAMPLE 14

4-((3-Ethyl-4-methyl-2-oxo-3-pyrroline-1-carboxamido)methyl)-6-(methylaminothiocarbonylaminosulfonyl)-7-methoxychroman

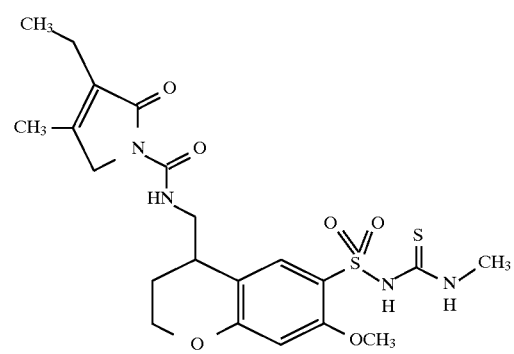

1.27 g (3 mmol) of 4-((3-ethyl-4-methyl-2-oxo-3-pyrroline-1-carboxamido)-methyl)-6-sulfamoyl-7-methoxychroman, 1.24 g (9 mmol) of finely powdered potassium carbonate and 0.292 g (4 mmol) of methyl isothiocyanate are suspended or dissolved in 12 ml of DMSO. The reaction mixture is stirred at 80° C. for 1 hour. The mixture is poured onto ice water and the product is precipitated by acidifying with hydrochloric acid. After filtering off with suction and drying, the crude product is purified by chromatography on silica gel (eluent : methylene chloride/glacial acetic acid 9:1). Melting point: 115° C.

Preparation of the starting compound 4-((3-ethyl-4-methyl-2-oxo-3-pyrroline-1-carboxamido)methyl)-6-sulfamoyl-7-methoxychroman

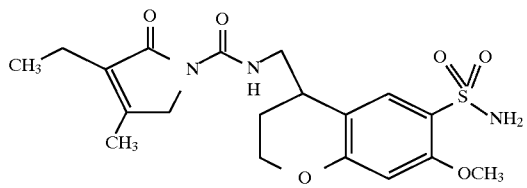

7.33 g (38 mmol) of 4-aminomethyl-7-methoxychroman are dissolved in 50 ml of tetrahydrofuran. 6.16 g (38 mmol) of N,N'-carbonyldiimidazole are added. The mixture is stirred at room temperature for one hour and then evaporated in vacuo. 4.76 g (38 mmol) of 3-ethyl-4-methyl-2-oxo-3-pyrroline are added to the residue and the mixture is heated at 160°–170° C. for 2 hours. It is chromatographed on silica gel using the eluent ethyl acetate/petroleum ether (3:1) and 4-((3-ethyl-4-methyl-2-oxo-3-pyrroline-1-carboxamido) methyl)-7-methoxychroman of melting point 115° C. is obtained. This product is introduced in the customary manner into chlorosulfonic acid cooled to −15° C. The mixture is allowed to come to room temperature and is stirred for one hour. After customary working up, the sulfochloride is converted into the sulfonamide as described in Example 1. 4-((3-Ethyl-4-methyl-2-oxo-3-pyrroline-1-carboxamido) methyl)-6-sulfamoyl-7-methoxychroman has a melting point of 235°–236° C.

EXAMPLE 15

4-((3-Ethyl-4-methyl-2-oxo-3-pyrroline-1-carboxamido) methyl)-6-(ethylaminothiocarbonylaminosulfonyl)-7-methoxychroman

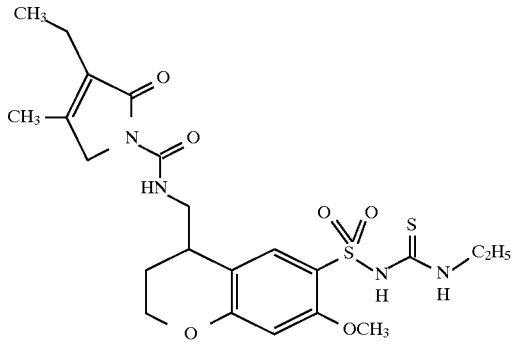

4-((3-Ethyl-4-methyl-2-oxo-3-pyrroline-1-carboxamido) methyl)-6-(ethylaminothio-carbonylaminosulfonyl)-7-methoxychroman is prepared analogously to Example 14 from 4-((3-ethyl-4-methyl-2-oxo-3-pyrroline-1-carboxamido) methyl)-6-sulfamoyl-7-methoxychroman and ethyl isothiocyanate. Melting point: 147° C.

EXAMPLE 16

4-((3-Ethyl-4-methyl-2-oxo-3-pyrroline-1-carboxamido) methyl)-6-(n-propylaminothiocarbonylaminosulfonyl)-7-methoxychroman

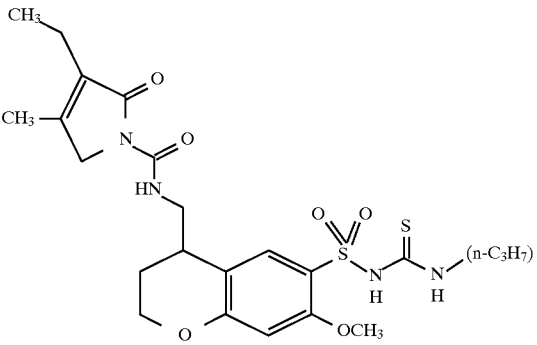

4-((3-Ethyl-4-methyl-2-oxo-3-pyrroline-1-carboxamido) methyl)-6-(n-propylaminothiocarbonylaminosulfonyl)-7-methoxychroman is prepared as described in Example 14 from 4-((3-ethyl-4-methyl-2-oxo-3-pyrroline-1-carboxamido) methyl)-6-sulfamoyl-7-methoxychroman and n-propyl isothiocyanate. Melting point: 96°–98° C.

EXAMPLE 17

4-((3-Ethyl-4-methyl-2-oxo-3-pyrroline-1-carboxamido) methyl)-6-(isopropylaminothiocarbonylaminosulfonyl)-7-methoxychroman

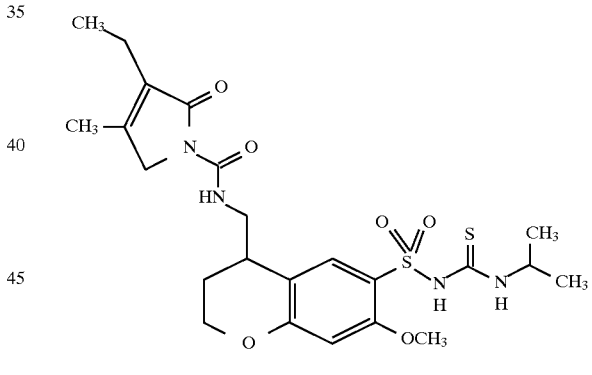

4-((3-Ethyl-4-methyl-2-oxo-3-pyrroline-1-carboxamido) methyl)-6-(isopropylaminothiocarbonylaminosulfonyl)-7-methoxychroman is synthesized following Example 14 starting from 4-((3-ethyl-4-methyl-2-oxo-3-pyrroline-1-carboxamido)methyl)6-sulfamoyl-7-methoxychroman and isopropyl isothiocyanate. Melting point: 153° C.

EXAMPLE 18

4-((3-Ethyl-4-methyl-2-oxo-3-pyrroline-1-carboxamido) methyl)-6-(methylamino-carbonylaminosulfonyl)-7-methoxychroman

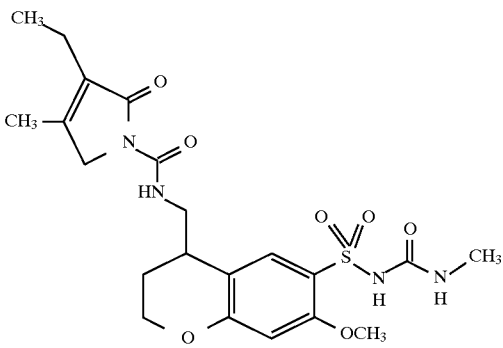

0.5 g of 4-((3-ethyl-4-methyl-2-oxo-3-pyrroline-1-carboxamido) methyl)-6-(methylaminothiocarbonylaminosulfonyl)-7-methoxychroman (Example 14) is dissolved in 10 ml of cold 0.5N sodium hydroxide solution. 0.5 ml of 37% strength hydrogen peroxide solution are added in the cold (–4 to 0° C.) and the mixture is stirred at 0° C. for 1 hour. The product is precipitated by addition of 2N HCl. The crude product is purified by chromatography on silica gel (Eluent: methylene chloride/glacial acetic acid 9:1). Melting point: 211° C.

EXAMPLE 19

4-((3-Ethyl-4-methyl-2-oxo-3-pyrroline-1-carboxamido) methyl)-6-(ethylaminocarbonylaminosulfonyl)-7-methoxychroman

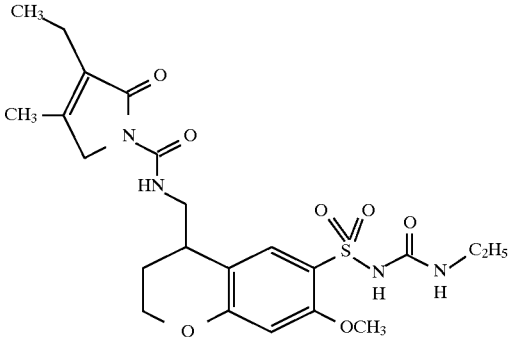

4-((3-Ethyl-4-methyl-2-oxo-3-pyrroline-1-carboxamido) methyl)-6-(ethylaminothiocarbonylaminosulfonyl)-7-methoxychroman is obtained analogously to Example 18 by oxidation of 4-((3-ethyl-4-methyl-2-oxo-3-pyrrolidinyl-1-carboxamido) methyl)-6-(ethylaminothiocarbonylaminosulfonyl)-7-methoxychroman using 37% strength hydrogen peroxide solution. Melting point: 188°–189° C.

EXAMPLE 20

4-((3-Ethyl-4-methyl-2-oxo-3-pyrroline-1-carboxamido) methyl)-6-(methylaminothiocarbonyl aminosulfonyl)-7-ethoxychroman

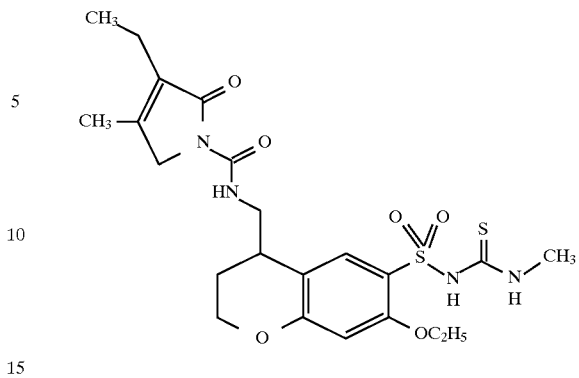

4-((3-Ethyl-4-methyl-2-oxo-3-pyrroline-1-carboxamido) methyl)-6-(methylaminothiocarbonylaminosulfonyl)-7-ethoxychroman is synthesized analogously to Example 14 from 4-((3-ethyl-4-methyl-2-oxo-3-pyrroline-1-carboxamido) methyl)-6-sulfamoyl-7-ethoxychroman and methyl isothiocyanate. Melting point: 178° C.

Preparation of the starting compound 4-((3-ethyl-4-methyl-2-oxo-3-pyrroline-1-carboxamido) methyl)-6-sulfamoyl-7-ethoxychroman

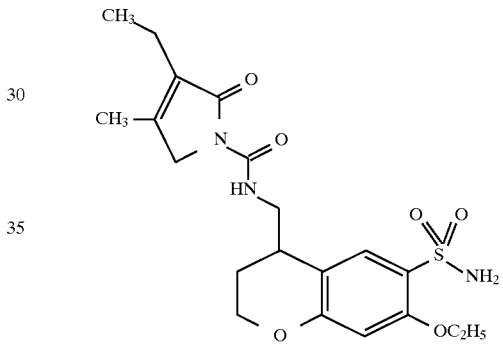

9.5 ml (0.1 mol) of boron tribromide are added dropwise to a solution of 10.6 g (0.025 mol of 4-((3-ethyl-4-methyl-2-oxo-3-pyrroline-1-carboxamido) methyl)-6-sulfamoyl-7-methoxychroman in 75 ml of methylene chloride cooled to –10° C. After standing overnight at 20° C., the excess boron tribromide is destroyed after cooling to –10° C. by cautious dropwise addition of methanol. The mixture is then introduced into ice/water and extracted several times with methylene chloride. The combined methylene chloride extracts are dried, evaporated and recrystallized from methanol. 4-((3-Ethyl-4-methyl-2-oxo-3-pyrroline-1-carboxamido) methyl)-6-sulfamoyl-7-hydroxychroman of melting point 175° C. is obtained.

2.16 ml (0.027 mol) of ethyl iodide are added to a suspension of 9 g (0.022 mol) of 4-((3-ethyl-4-methyl-2-oxo-3-pyrroline-1-carboxamido)-methyl)-6-sulfamoyl-7-hydroxychroman and 6.1 g (0.044 mol) of potassium carbonate in 60 ml of acetone. After stirring under reflux for three hours, the mixture is introduced into ice/water and cautiously acidified with concentrated hydrochloric acid. The precipitate is filtered off with suction, washed several times with cold water, dried and recrystallized from ethanol/DMF. 4-((3-Ethyl-4-methyl-2-oxo-3-pyrroline-1-carboxamido)-methyl)-6-sulfamoyl-7-ethoxychroman of melting point 192° C. is obtained.

EXAMPLE 21

4-((3-Ethyl-4-methyl-2-oxo-3-pyrroline-1-carboxamido)methyl)-6-(ethylaminothiocarbonylaminosulfonyl)-7-ethoxychroman

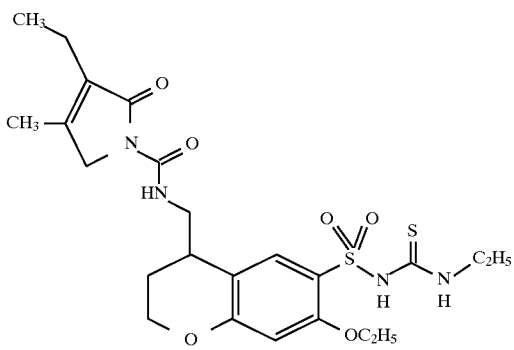

4-((3-Ethyl-4-methyl-2-oxo-3-pyrroline-1-carboxamido)methyl)-6-(ethylaminothiocarbonylaminosulfonyl)-7-ethoxychroman is synthesized analogously to Example 14, starting from 4-((3-ethyl-4-methyl-2-oxo-3-pyrroline-1-carboxamido) methyl)-6-sulfamoyl-7-ethoxychroman and ethyl isothiocyanate. Melting point: 178°–180° C.

EXAMPLE 22

4-((3-Ethyl-4-methyl-2-oxo-3-pyrroline-1-carboxamido)methyl)-6-(methylaminocarbonylaminosulfonyl)-7-ethoxychroman

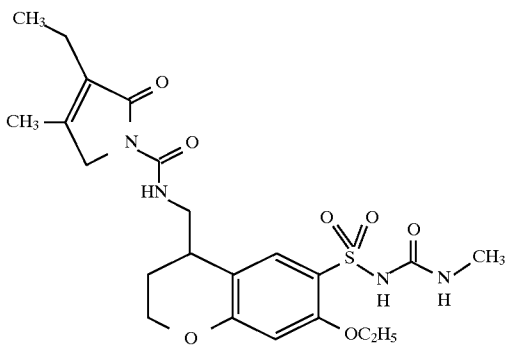

4-((3-Ethyl-4-methyl-2-oxo-3-pyrroline-1-carboxamido)methyl)-6-(methylaminocarbonylaminosulfonyl)-7-ethoxychroman is prepared analogously to Example 18 by oxidation of 4-((3-ethyl-4-methyl-2-oxo-3-pyrroline-1-carboxamido) methyl)-6-(methylaminothiocarbonylaminosulfonyl)-7-ethoxychroman using hydrogen peroxide solution. Melting point: 187°–188° C.

EXAMPLE 23

4-((3-Ethyl-4-methyl-2-oxo-3-pyrroline-1-carboxamido)methyl)-6-(ethylaminocarbonylaminosulfonyl)-7-ethoxychroman

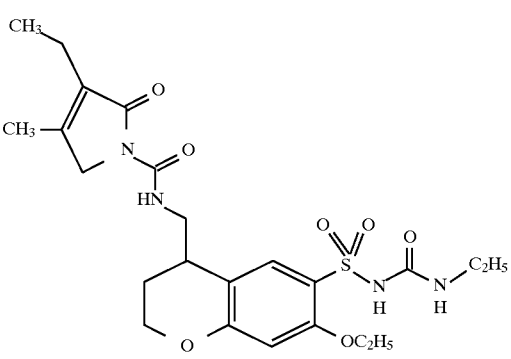

4-((3-Ethyl-4-methyl-2-oxo-3-pyrroline-1 -carboxamido)methyl)-6-(ethylamino-carbonylaminosulfonyl)-7-ethoxychroman is obtained analogously to Example 18 by oxidation of 4-((3-ethyl-4-methyl-2-oxo-3-pyrroline-1-carboxamido)methyl)-6-(ethylaminothiocarbonylaminosulfonyl)-7-ethoxychroman using hydrogen peroxide solution. Melting point: 175° C.

EXAMPLE 24

(+)-4-(5-Chloro-2-methoxybenzamidomethyl)-6-(methylaminocarbonylaminosulfonyl)-7-methoxychroman

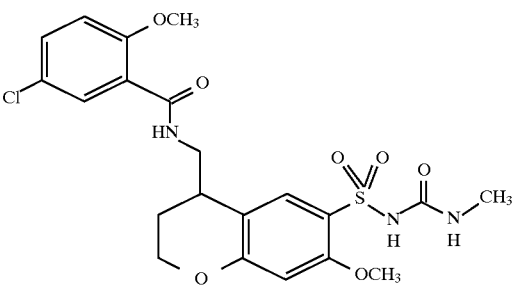

(+)-4-(5-Chloro-2-methoxybenzamidomethyl)-6-(methylaminocarbonylaminosulfonyl)-7-methoxychroman is prepared analogously to Example 1 from optically active 4-(5-chloro-2-methoxybenzamidomethyl)-6-sulfamoyl-7-methoxychroman and N-methyltrichloroacetamide. Melting point: 242° C.; $[\alpha]_D^{20}$: +63.4° (c=1, DMF); HPLC: ee 100%.

For the synthesis of the starting compound, which is prepared as described in Example 1, the dextrorotatory mandelate of 4-aminomethyl-7-methoxychroman (physicochemical data of the mandelate: melting point 144° C.; $[\alpha]_D^{20}$: +57.5° (c=1, H$_2$O); HPLC: ee 93.8%) is employed.

EXAMPLE 25

(+)-4-(5-Chloro-2-methoxy-benzamidomethyl)-6-(methylaminothiocarbonyl-aminosulfonyl)-7-methoxychroman

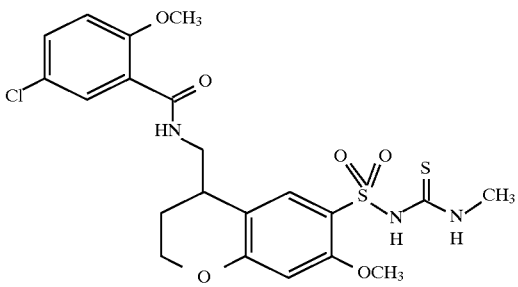

(+)-4-(5-Chloro-2-methoxy-benzamidomethyl)-6-(methylaminothiocarbonylaminosulfonyl)-7-methoxychroman is prepared as described in Example 4 from optically active 4-(5-chloro-2-methoxy-benzamidomethyl)-6-sulfamoyl-7-methoxychroman and methyl isothiocyanate. Melting point: 201° C.; $[\alpha]_D^{20}$: +47.2° (c=1, DMF); HPLC: ee 88.1%.

EXAMPLE 26

(−)-4-(5-Chloro-2-methoxybenzamidomethyl)-6-(methylaminocarbonylaminosulfonyl)-7-methoxychroman

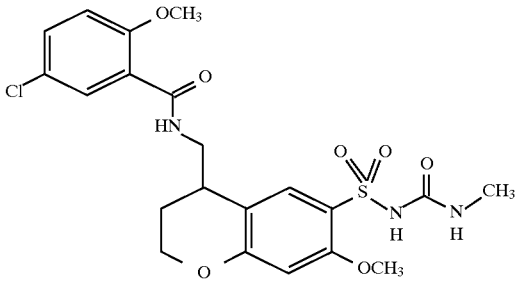

(−)-4-(5-Chloro-2-methoxy-benzamidomethyl)-6-(methylaminocarbonyl-aminosulfonyl)-7-methoxychroman is prepared analogously to Example 1 from optically active 4-(5-chloro-2-methoxybenzamido methyl)-6-sulfamoyl-7-methoxychroman and N-methyltrichloroacetamide. Melting point: 239° C.; $[\alpha]_D^{20}$: −59.8° (c=1, DMF); HPLC: ee 98.5%.

For the synthesis of the starting compound, which is prepared as described in Example 1, the levorotatory mandelate of 4-aminomethyl-7-methoxychroman (physicochemical data of the mandelate: melting point: 147°–148° C.; $[\alpha]_D^{20}$: −59.5° (c=1, H$_2$O); HPLC: ee 99.1 %) is employed.

EXAMPLE 27

(−)-4-(5-Chloro-2-methoxybenzamidomethyl)-6-(methylaminothiocarbonylaminosulfonyl)-7-methoxychroman

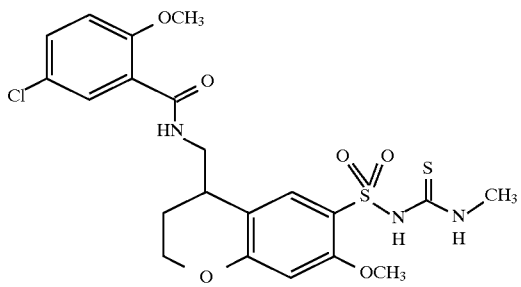

(−)-4-(5-Chloro-2-methoxybenzamidomethyl)-6-(methylaminothiocarbonyl-aminosulfonyl)-7-methoxychroman is prepared as described in Example 4 from optically active 4-(5-chloro-2-methoxybenzamidomethyl)-6-sulfamoyl-7-methoxychroman and methyl isothiocyanate. Melting point: 202° C., $[\alpha]_D^{20}$: −64.5° (c=1, DMF); HPLC: ee 97.9%.

Pharmacological data

Using the following model, the therapeutic properties of the compounds of the formula I can be demonstrated.

Action potential duration on the papillary muscle of the guineapig:

(a) Introduction

ATP deficiency states, such as are observed during ischemia in the cardiac muscle cell, lead to a shortening of the action potential duration. They count as one of the causes of so-called reentry arrhythmias, which can cause sudden heart death. The opening of ATP-sensitive K channels by the lowering of ATP is regarded here as causal.

(b) Method

To measure the action potential, a standard microelektrode technique is employed. For this, guinea-pigs of both sexes are killed by a blow to the head, the hearts are removed and the papillary muscles are separated out and suspended in an organ bath. The organ bath is irrigated with Ringer solution (0.9% NaCl, 0.048% KCl, 0.024% CaCl$_2$, 0.02% NaHCO$_3$, and 0.1% glucose) and aerated with a mixture of 95% oxygen and 5% carbon dioxide at a temperature of 36° C. The muscle is stimulated by means of an electrode with square-wave impulses of 1 V and 1 ms duration and a frequency of 2 Hz. The action potential is derived and recorded by an intracellularly inserted glass microelectrode which is filled with 3M KCl solution. The substances to be tested are added to the Ringer solution in a concentration of 2.2·10$^{-6}$ mol per liter. The action potential is shown amplified on an oscilloscope using an amplifier from Hugo Sachs. The duration of the action potential is determined as a degree of repolarization of 95% (APD$_{95}$). Action potential reductions are induced by addition of a 1 μM strength solution of the potassium channel opener Hoe 234 (Rilmakalim) (W. Linz, E. Klaus, U. Albus, R. H. A. Becker, D. Mania, H. C. Englert, B. A. Schölkens, Arzneimittelforschung/Drug Research, Volume 42 (II), 1992, pp. 1180–1185). Test substances were added to the bath solution as stock solutions in propanediol. The values indicated relate to measurements 30 min after addition. The control is regarded as the APD$_{95}$ in the presence of HOE 234 and in the absence of the test substance.

(c) Results
The following values were measured:

| Measurement | APD$_{95}$-HOE 234[a] [ms] |
|---|---|
| Control | <40 |
| Example 1 | 109 ± 1 |
|  | (164 ± 18) |
|  | n = 3 |
| Example 2 | 96 ± 35 |
|  | (141 ± 2) |
|  | n = 3 |
| Example 3 | 138 ± 8 |
|  | (172 ± 11) |
|  | n = 3 |
| Example 4 | 144 ± 9 |
|  | (181 ± 2) |
|  | n = 3 |
| Example 24 | 70 ± 7 |
|  | (169 ± 10) |
|  | n = 3 |
| Example 25 | 123 ± 19 |
|  | (158 ± 4) |
|  | n = 3 |
| Example 26 | 140 ± 7 |
|  | (171 ± 14) |
|  | n = 3 |
| Example 27 | 169 ± 16 |
|  | (164 ± 23) |
|  | n = 3 |

[a] the measured values (mean value of n experiments) are followed by the corresponding blank values in brackets. The blank values are the APD$_{95}$ values at the start of the experiment without HOE 234 and test substance in the Ringer solution.

We claim:

1. A chromanylsulfonyl(thio)urea of the formula I

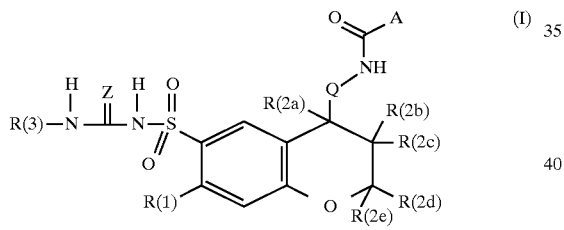

or a physiologically tolerable salt thereof, in which:

R(1) is hydrogen, alkyl having 1 to 4 carbon atoms, alkoxy having 1 to 4 carbon atoms, fluorine, chlorine, bromine, iodine, CF$_3$, NH$_2$, NH-alkyl having 1 to 4 carbon atoms, N(alkyl)$_2$ having 1 to 4 carbon atoms in the identical or different alkyl radicals, or S-alkyl having 1 to 4 carbon atoms;

R(2a) is hydrogen or alkyl having 1 or 2 carbon atoms;

R(2b) and R(2d), which are identical or different, are hydrogen, alkyl having 1 or 2 carbon atoms, unsubstituted phenyl, substituted phenyl, unsubstituted benzyl or benzyl substituted in the phenyl radical, up to three identical or different substituents, selected from the group consisting of halogen, alkyl having 1 or 2 carbon atoms and alkoxy having 1 or 2 carbon atoms being present as substituents in phenyl radicals;

R(2c) and R(2e), which are identical or different, are hydrogen or alkyl having 1 or 2 carbon atoms;

R(3) is hydrogen, alkyl having 1, 2, 3 or 4 carbon atoms, cycloalkyl having 3, 4, 5 or 6 ring carbon atoms, CH$_2$-cycloalkyl having 3, 4, 5 or 6 ring carbon atoms, or CF$_3$;

Q is (CH$_2$)$_n$;

n is 1 or 2;

Z is sulfur or oxygen;

A is phenyl which is unsubstituted or substituted by up to three identical or different substituents selected from the group consisting of hydrogen, halogen, alkyl having 1 or 2 carbon atoms and alkoxy having 1 or 2 carbon atoms;

or

A is the radical of a saturated or unsaturated lactam of the formula

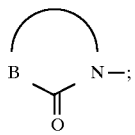

B is alkenylene or alkylene having 3, 4, 5 or 6 carbon atoms, which is unsubstituted or is substituted by up to three identical or different alkyl groups having 1, 2, 3 or 4 carbon atoms;

or

A is the radical of a bicyclic system of the formula

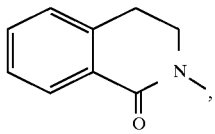

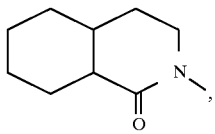

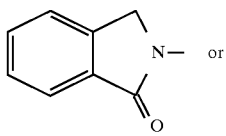 or

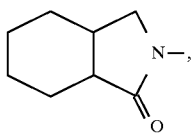

2. A compound of the formula I as claimed in claim 1, or a physiologically tolerable salt thereof, in which:

R(1) is hydrogen, alkyl having 1 or 2 carbon atoms, alkoxy having 1 to 4 carbon atoms, fluorine, chlorine, bromine, iodine or CF$_3$;

R(2a), R(2b) and R(2d), which are identical or different, are hydrogen or alkyl having 1 or 2 carbon atoms;

R(2c) and R(2e) are hydrogen;

R(3) is hydrogen or alkyl having 1, 2, 3 or 4 carbon atoms;

Q is (CH$_2$)$_n$;

n is 1 or 2;

Z is sulfur or oxygen;

A is phenyl, which is unsubstituted or substituted by up to three identical or different substituents selected from the group consisting of halogen, alkyl having 1 or 2 carbon atoms and alkoxy having 1 or 2 carbon atoms or A is the radical of a saturated or unsaturated lactam of the formula

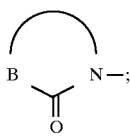

B is alkenylene or alkylene having 3, 4, 5 or 6 carbon atoms, which is unsubstituted or is substituted by up to three identical or different alkyl groups having 1, 2, 3 or 4 carbon atoms;

or

A is the radical of a bicyclic system of the formula

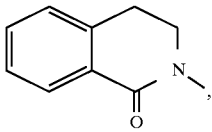

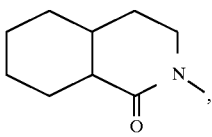

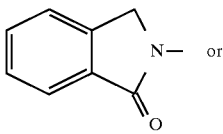

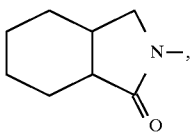

3. A compound of the formula I as claimed in claim 1, or a physiologically tolerable salt thereof, in which:
R(1) is hydrogen, alkyl having 1 or 2 carbon atoms, alkoxy having 1 or 2 carbon atoms, fluorine, chlorine, bromine, iodine or CF$_3$;
R(2a), R(2b), R(2c), R(2d) and R(2e) are hydrogen;
R(3) is hydrogen or alkyl having 1, 2, 3 or 4 carbon atoms;
Q is (CH$_2$)$_n$;
n is 1 or 2;
Z is sulfur or oxygen;
A is phenyl, which is unsubstituted or substituted by up to three identical or different substituents selected from the group consisting of halogen, alkyl having 1 or 2 carbon atoms and alkoxy having 1 or 2 carbon atoms;

or

A is the radical of a saturated or unsaturated lactam of the formula

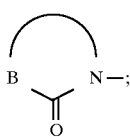

B is alkenylene or alkylene having 3, 4, 5 or 6 carbon atoms, which is unsubstituted or is substituted by up to three identical or different alkyl groups having 1, 2, 3 or 4 carbon atoms;

or

A is the radical of a bicyclic system of the formula

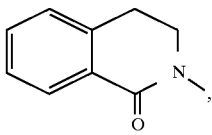

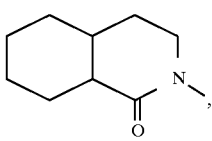

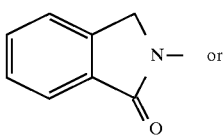

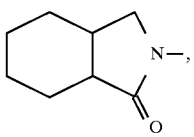

4. A compound of the formula I according to claim 1, or a physiologically tolerable salt thereof, in which:
R(1) is hydrogen, alkyl having 1 or 2 carbon atoms or alkoxy having 1 or 2 carbon atoms;
R(2a), R(2b), R(2c), R(2d) and R(2e) are hydrogen;
R(3) is hydrogen or alkyl having 1, 2, 3 or 4 carbon atoms;
Q is (CH$_2$)$_n$;
n is 1 or 2;
Z is sulfur;
A is phenyl, which is unsubstituted or substituted by up to three identical or different substituents selected from the group consisting of hydrogen, halogen, alkyl having 1 or 2 carbon atoms and alkoxy having 1 or 2 carbon atoms;

or

A is the radical of a saturated or unsaturated lactam of the formula

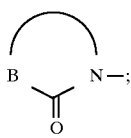

B is alkenylene or alkylene having 3, 4, 5 or 6 carbon atoms, which is unsubstituted or is substituted by up to three identical or different alkyl groups having 1, 2, 3 or 4 carbon atoms;

or

A is the radical of a bicyclic system of the formula

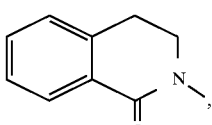

-continued

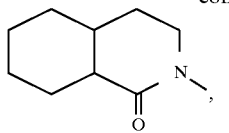

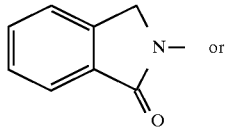

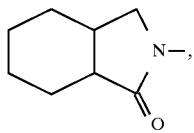

5. A compound of the formula I according to claim 1, or a physiologically tolerable salt thereof, in which:
R(1) is hydrogen, alkyl having 1 or 2 carbon atoms or alkoxy having 1 or 2 carbon atoms;
R(2a), R(2b), R(2c), R(2d) and R(2e) are hydrogen;
R(3) is hydrogen, methyl or ethyl;
Q is $(CH_2)_n$;
n is 1 or 2;
Z is sulfur;
A is phenyl, which is unsubstituted or substituted by up to three identical or different substituents selected from the group consisting of halogen, alkyl having 1 or 2 carbon atoms and alkoxy having 1 or 2 carbon atoms;
or
A is the radical of a saturated or unsaturated lactam of the formula

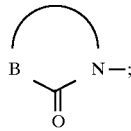

B is alkenylene or alkylene having 3, 4, 5 or 6 carbon atoms, which is unsubstituted or is substituted by up to three identical or different alkyl groups having 1, 2, 3 or 4 carbon atoms.

6. A compound of the formula I according to claim 1, or a physiologically tolerable salt thereof, in which:
R(1) is hydrogen, alkyl having 1 or 2 carbon atoms or alkoxy having 1 or 2 carbon atoms;
R(2a), R(2b), R(2c), R(2d) and R(2e) are hydrogen;
R(3) is hydrogen, methyl or ethyl;
Q is $CH_2$;
n is 1 or 2;
Z is sulfur;
A is phenyl, which is unsubstituted or substituted by up to three identical or different substituents selected from the group consisting halogen, alkyl having 1 or 2 carbon atoms and alkoxy having 1 or 2 carbon atoms.

7. A compound of the formula I according to claim 1, or a physiologically tolerable salt thereof, in which:
R(1) is hydrogen, alkyl having 1 or 2 carbon atoms or alkoxy having 1 or 2 carbon atoms;
R(2a), R(2b), R(2c), R(2d) and R(2e) are hydrogen;

R(3) is hydrogen or alkyl having 1, 2, 3 or 4 carbon atoms;
Q is $(CH_2)_n$;
n is 1 or 2;
Z is oxygen;
A is phenyl, which is unsubstituted or substituted by up to three identical or different substituents selected from the group consisting halogen, alkyl having 1 or 2 carbon atoms and alkoxy having 1 or 2 carbon atoms;
or
A is the radical of a saturated or unsaturated lactam of the formula

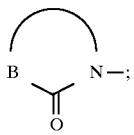

B is alkenylene or alkylene having 3, 4, 5 or 6 carbon atoms which is unsubstituted or is substituted by up to three identical or different alkyl groups having 1, 2, 3 or 4 carbon atoms;
or
A is the radical of a bicyclic system of the formula

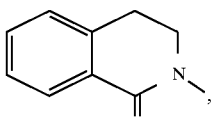

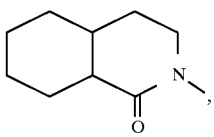

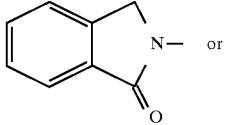

8. A compound of the formula I according to claim 1, or a physiologically tolerable salt thereof, in which:
R(1) is hydrogen, alkyl having 1 or 2 carbon atoms or alkoxy having 1 or 2 carbon atoms;
R(2a), R(2b), R(2c), R(2d) and R(2e) are hydrogen;
R(3) is hydrogen, methyl or ethyl;
Q is $(CH_2)_n$;
n is 1 or 2;
Z is oxygen;
A is phenyl, which is unsubstituted or substituted by up to three identical or different substituents selected from the group consisting halogen, alkyl having 1 or 2 carbon atoms and alkoxy having 1 or 2 carbon atoms;
or
A is the radical of a saturated or unsaturated lactam of the formula

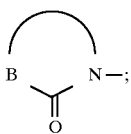

B is alkenylene or alkylene having 3, 4, 5 or 6 carbon atoms, which is unsubstituted or is substituted by up to three identical or different alkyl groups having 1, 2, 3 or 4 carbon atoms.

9. A compound of the formula I according to claim 1, or a physiologically tolerable salt thereof, in which:
R(1) is hydrogen, alkyl having 1 or 2 carbon atoms or alkoxy having 1 or 2 carbon atoms;
R(2a), R(2b), R(2c), R(2d) and R(2e) are hydrogen;
R(3) is hydrogen, methyl or ethyl;
Q is $CH_2$;
n is 1 or 2;
Z is oxygen;
A is phenyl, which is unsubstituted or substituted by up to three identical or different substituents selected from the group consisting halogen, alkyl having 1 or 2 carbon atoms and alkoxy having 1 or 2 carbon atoms.

10. A compound according to claim 1, which is 4-(5-chloro-2-methoxybenzamidomethyl)-6-(methylaminocarbonylaminosulfonyl)-7-methoxychroman.

11. A compound according to claim 1, which is 4-(5-chloro-2-methoxybenzamidomethyl)-6-(ethylaminocarbonylaminosulfonyl)-7-methoxychroman.

12. A compound according to claim 1, which is 4-(5-chloro-2-methoxybenzamidomethyl)-6-(n-propylaminocarbonylaminosulfonyl)-7-methoxychroman.

13. A compound according to claim 1, which is 4-(5-chloro-2-methoxybenzamidomethyl)-6-(methylaminothiocarbonylaminosulfonyl)-7-methoxychroman.

14. A compound according to claim 1, which is 4-(5-chloro-2-methoxybenzamidomethyl-6-(ethylaminothiocarbonylaminosulfonyl)-7-methoxychroman.

15. A compound according to claim 1, which is 4-(5-chloro-2-methoxybenzamidomethyl)-6-(n-propylaminothiocarbonylaminosulfonyl)-7-methoxychroman.

16. A compound according to claim 1, which is 4-(5-chloro-2-methoxybenzamidomethyl)-6-(isopropylaminothiocarbonylaminosulfonyl)-7-methoxychroman.

17. A compound according to claim 1, which is 4-(5-chloro-2-methoxybenzamidomethyl)-6-(n-butylaminothiocarbonylaminosulfonyl)-7-methoxychroman.

18. A compound according to claim 1, which is 4-(5-chloro-2-methoxybenzamidomethyl)-6-(methylaminocarbonylaminosulfonyl)-7-ethoxychroman.

19. A compound according to claim 1, which is 4-(5-chloro-2-methoxybenzamidomethyl)-6-(methylaminothiocarbonylaminosulfonyl)-7-methoxychroman.

20. A compound according to claim 1, which is 4-(5-fluoro-2-methoxybenzamidomethyl)-6-(methylaminocarbonylaminosulfonyl)-7-methoxychroman.

21. A compound according to claim 1, which is 4-(5-fluoro-2-methoxybenzamidomethyl)-6-(methylaminothiocarbonylaminosulfonyl)-7-methoxychroman.

22. A compound according to claim 1, which is 4-(5-fluoro-2-methoxybenzamidomethyl)-6-(ethylaminothiocarbonylaminosulfonyl)-7-methoxychroman.

23. A compound according to claim 1, which is 4-((3-ethyl-4-methyl-2-oxo-3-pyrroline-1-carboxamido)methyl)-6-(methylaminothiocarbonylaminosulfonyl)-7-methoxychroman.

24. A compound according to claim 1, which is 4-((3-ethyl-4-methyl-2-oxo-3-pyrroline-1-carboxamido)methyl)-6-(ethylaminothiocarbonylaminosulfonyl)-7-methoxychroman.

25. A compound according to claim 1, which is 4-((3-ethyl-4-methyl-2-oxo-3-pyrroline-1-carboxamido)methyl)-6-(n-propylaminothiocarbonylaminosulfonyl)-7-methoxychroman.

26. A compound according to claim 1, which is 4-((3-ethyl-4-methyl-2-oxo-3-pyrroline-1-carboxamido)methyl)-6-(isopropylaminothiocarbonylaminosulfonyl)-7-methoxychroman.

27. A compound according to claim 1, which is 4-((3-ethyl-4-methyl-2-oxo-3-pyrroline-1-carboxamido)methyl)-6-(methylamino-carbonylaminosulfonyl)-7-methoxychroman.

28. A compound according to claim 1, which is 4-((3-ethyl-4-methyl-2-oxo-3-pyrroline-1-carboxamido)methyl)-6-(ethylaminocarbonylaminosulfonyl)-7-methoxychroman.

29. A compound according to claim 1, which is 4-((3-ethyl-4-methyl-2-oxo-3-pyrroline-1-carboxamido)methyl)-6-(methylaminothiocarbonylaminosulfonyl)-7-ethoxychroman.

30. A compound according to claim 1, which is 4-((3-ethyl-4-methyl-2-oxo-3-pyrroline-1-carboxamido)methyl)-6-(ethylaminothiocarbonylaminosulfonyl)-7-ethoxychroman.

31. A compound according to claim 1, which is 4-((3-ethyl-4-methyl-2-oxo-3-pyrroline-1-carboxamido)methyl)-6-(methylaminocarbonylaminosulfonyl)-7-ethoxychroman.

32. A compound according to claim 1, which is 4-((3-ethyl-4-methyl-2-oxo-3-pyrroline-1-carboxamido)methyl)-6-(ethylaminocarbonylaminosulfonyl)-7-ethoxychroman.

33. A compound according to claim 1, which is (+)-4-(5-chloro-2-methoxybenzamidomethyl)-6-(methylaminocarbonylaminosulfonyl)-7-methoxychroman.

34. A compound according to claim 1, which is (+)-4-(5-chloro-2-methoxy-benzamidomethyl)-6-(methylaminothiocarbonylaminosulfonyl)-7-methoxychroman.

35. A compound according to claim 1, which is (–)-4-(5-chloro-2-methoxybenzamidomethyl)-6-(methylaminocarbonylaminosulfonyl)-7-methoxychroman.

36. A compound according to claim 1, which is (–)-4-(5-chloro-2-methoxybenzamidomethyl)-6-(methylaminothiocarbonylaminosulfonyl)-7-methoxychroman.

37. A process for the preparation of a compound of the formula I as claimed in claim 1, which comprises reacting a sulfamoylchroman of the formula II

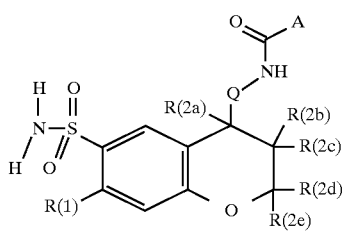

(II)

or its salt of the formula III

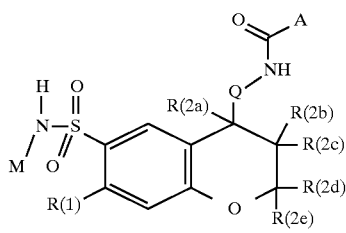

(III)

in which the radicals have the meanings indicated in claim 1, and M is a cation, with an R(3)-substituted isocyanate or isothiocyanate, an R(3)-substituted carbonic acid derivative or a trichloroacetamide which is R(3)-substituted on the nitrogen, in which R(3) has the meaning indicated in claim 1;

or, for the preparation of a compound of the formula I in which R(3) is hydrogen, reacting a compound of the formula II or III with a trialkylsilyliso(thio)cyanate or silicon tetraiso(thio)cyanate and cleaving the silicon-substituted chromanylsulfonyl(thio)urea primarily formed;

or, for the preparation of a compound of the formula I in which Z is oxygen, desulfurizing a compound of the formula I in which Z is sulfur;

or, for the preparation of a compound of the formula I in which Z is oxygen, reacting a compound of the formula VII

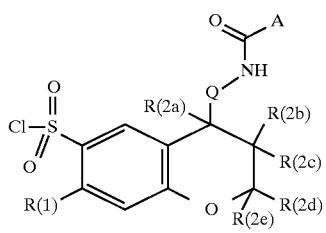

(VII)

in which the radicals have the meanings indicated in claim 1, with an R(3)-substituted urea or bis(trialkyl)silylurea, in which R(3) has the meaning indicated in claim 1;

or reacting a compound of the formula VII or of the formula IX

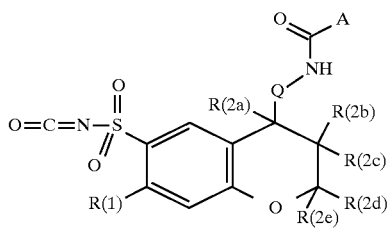

(VIII)

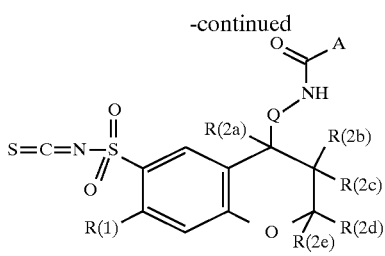

(IX)

in which the radicals have the meanings indicated in claim 1, with an amine of the formula R(3)—NH$_2$, in which R(3) has the meaning indicated in claim 1.

38. A pharmaceutical composition comprising a compound according to claim 1, or a physiologically tolerable salt thereof, in admixture with a suitable pharmaceutical carrier.

39. A method of treatment of a cardiac arrhythmia in a patient in need thereof comprising administering to the patient a therapeutically effective amount of a compound according to claim 1, or a physiologically tolerable salt thereof.

40. A method of preventing sudden heart death due to cardiac arrhythmia in a patient in need thereof, comprising administering to the patient an effective amount of a compound according to claim 1, or a physiologically tolerable salt thereof.

41. A method of treatment of an ischemic condition of the heart in a patient in need thereof comprising administering to the patient a therapeutically effective amount of a compound according to claim 1, or a physiologically tolerable salt thereof.

42. A method of treatment of weakened myocardial contraction in a patient in need thereof comprising administering to the patient a therapeutically effective amount of a compound according to claim 1, or a physiologically tolerable salt thereof.

43. A method of treatment for improving cardiac function after heart transplantation in a patient in need thereof comprising administering to the patient an therapeutically effective amount of a compound according to claim 1, or a physiologically tolerable salt thereof.

44. A method for the treatment of a disorder of the cardiovascular system, a cardiac arrhythmia, an ischemic condition of the heart, or weakened myocardial contraction force comprising administering to the patient a therapeutically effective amount of a compound according to claim 1, or a physiologically tolerable salt thereof.

45. The method as claimed in claim 40, wherein the patient is suffering from an ischemic condition of the heart.

46. A method for the prophylaxis of a cardiac arrhythmia or of sudden heart death due to cardiac arrhythmia in a patient in need thereof, comprising administering to the patient an effective amount of a compound according to claim 1, or a physiologically tolerable salt thereof.

47. The method as claimed in claim 46, wherein the patient is suffering from an ischemic condition of the heart.

* * * * *

UNITED STATES PATENT AND TRADEMARK OFFICE
CERTIFICATE OF CORRECTION

PATENT NO. : 5,811,448
DATED : September 22, 1998
INVENTOR(S) : Heinrich Christian Englert et al.

It is certified that error appears in the above-identified patent and that said Letters Patent is hereby corrected as shown below:

Claim 2, column 38,
Line 34, "$(CH_2),$;" should read -- $(CH_2)_n$; --.

Claim 6, column 39,
Line 61, "consisting halogen" should read -- consisting of halogen --.

Claim 7, column 40,
Line 8, "consisting halogen" should read -- consisting of halogen --.

Claim 8, column 40,
Line 63, "consisting halogen" should read -- consisting of halogen --.

Claim 9, column 41,
Line 26, "consisting halogen" should read -- consisting of halogen --.

Signed and Sealed this

Thirtieth Day of October, 2001

Attest:

*Attesting Officer*

NICHOLAS P. GODICI
*Acting Director of the United States Patent and Trademark Office*